(12) United States Patent
Dantas et al.

(10) Patent No.: US 12,247,196 B2
(45) Date of Patent: Mar. 11, 2025

(54) ENGINEERED MICROORGANISMS AND METHODS OF MAKING AND USING SAME

(71) Applicants: Washington University, St. Louis, MO (US); Vir Biotechnology, Inc., San Francisco, CA (US)

(72) Inventors: Gautam Dantas, St. Louis, MO (US); Suryang Kwak, St. Louis, MO (US); Herbert Virgin, St. Louis, MO (US)

(73) Assignee: Washington University, St. Louis, MO (US)

( * ) Notice: Subject to any disclaimer, the term of this patent is extended or adjusted under 35 U.S.C. 154(b) by 824 days.

(21) Appl. No.: 17/278,027

(22) PCT Filed: Sep. 20, 2019

(86) PCT No.: PCT/US2019/052044
§ 371 (c)(1),
(2) Date: Mar. 19, 2021

(87) PCT Pub. No.: WO2020/061389
PCT Pub. Date: Mar. 26, 2020

(65) Prior Publication Data
US 2022/0033764 A1     Feb. 3, 2022

Related U.S. Application Data

(60) Provisional application No. 62/733,896, filed on Sep. 20, 2018.

(51) Int. Cl.
*C12N 1/20* (2006.01)
*C12N 9/22* (2006.01)
(Continued)

(52) U.S. Cl.
CPC .............. *C12N 1/20* (2013.01); *C12N 9/22* (2013.01); *C12N 15/63* (2013.01); *C12R 2001/865* (2021.05)

(58) Field of Classification Search
CPC .. C12N 1/20; C12N 9/22; C12N 15/63; C12R 2001/865
See application file for complete search history.

(56) References Cited

U.S. PATENT DOCUMENTS 6,579,693 B1    6/2003  Bellamine et al.
11,466,075 B2 * 10/2022 Feng ................ G01N 33/56961
(Continued)

FOREIGN PATENT DOCUMENTS

CN      1454258 A       11/2003
WO   2006095345 A2      9/2006
(Continued)

OTHER PUBLICATIONS

Swift et al (Viruses. Jun. 12, 2015;7(6):3019-34) (Year: 2015).*
(Continued)

*Primary Examiner* — Thomas J. Visone
*Assistant Examiner* — Georgiana C Reglas
(74) *Attorney, Agent, or Firm* — Polsinelli PC

(57) ABSTRACT

The present disclosure provides for engineered microorganisms and methods of making and using same. The engineered microorganisms as described herein can have a surface display and can be useful as therapeutic agents (e.g., sponges) and biosensors.

27 Claims, 23 Drawing Sheets

Specification includes a Sequence Listing.

(51) Int. Cl.
  *C12N 15/63* (2006.01)
  *C12R 1/865* (2006.01)

(56) References Cited

U.S. PATENT DOCUMENTS

| | | | |
|---|---|---|---|
| 2004/0170970 | A1 | 9/2004 | Varshavsky et al. |
| 2010/0303777 | A1 | 12/2010 | De Creus et al. |
| 2011/0150907 | A1 | 6/2011 | Seegers et al. |
| 2012/0171188 | A1 | 7/2012 | Loessner et al. |
| 2014/0193830 | A1 | 7/2014 | Schmidt et al. |
| 2016/0024484 | A1 | 1/2016 | Lim et al. |
| 2016/0040157 | A1 | 2/2016 | Hufton et al. |
| 2018/0037898 | A1 | 2/2018 | Ring et al. |

FOREIGN PATENT DOCUMENTS

| | | | |
|---|---|---|---|
| WO | 2009005869 | A2 | 1/2009 |
| WO | 2009139985 | A2 | 11/2009 |
| WO | 2009139985 | A3 | 1/2010 |

OTHER PUBLICATIONS

Tanaka et al (Journal of Biotechnology 145 (2010) 79-83) (Year: 2010).*
Brophy et al (Nat Methods. May 2014 ; 11(5): 508-520) (Year: 2014).*
Orchard et al (Science. Aug. 26, 2016;353(6302):933-6) (Year: 2016).*
Schmelcher et al (Future Microbiol. Oct. 2012;7(10):1147-71) (Year: 2012).*
Lood et al (Antimicrob Agents Chemother. Jun. 2014;58(6):3073-84) (Year: 2014).*
Gu et al (Curr Microbiol (2011) 63:538-542) (Year: 2011).*
Caravalho et al (BMC Microbiology 2010, 10:232) (Year: 2010).*
Liu et al (Appl Environ Microbiol. Apr. 4, 2016;82(8):2280-2287) (Year: 2016).*
Curran et al (Metab Eng. Sep. 2013 ; 19: 88-97) (Year: 2013).*
Douradinha et al (Bioengineered. Jan.-Feb. 2014;5(1):21-9) (Year: 2014).*
Flagfelt et al (Yeast 2009; 26: 545-551) (Year: 2009).*
Ananphongmanee V., et al., "Yeast Surface Display of Two Proteins Previously Shown to Be Protective Against White Spot Syndrome Virus (WSSV) in Shrimp," PLoS One, Jun. 17, 2015, vol. 10, No. 6, pp. 1-14.
International Preliminary Report on Patentability for International Application No. PCT/US2019/052044, mailed Apr. 1, 2021, 12 pages.
International Search Report and Written Opinion for International Application No. PCT/US2019/052044, mailed Dec. 27, 2019, 16 pages.
Lodder A.L., et al., "Characterization of the Wsc1 Protein, a Putative Receptor in the Stress Response of *Saccharomyces cerevisiae*," Genetics, Aug. 1, 1999, vol. 152, pp. 1487-1499.
Office Action for Eurasian Patent Application No. 202192317, dated May 26, 2023, 7 pages.
Straede A., et al., "Functional Analyses of the Extra- and Intracellular Domains of the Yeast Cell Wall Integrity Sensors Mid2 and Wsc1," FEBS Letters, 2007, vol. 581, pp. 4495-4500.
Dirnberger D., et al., "A Small-Molecule-Protein Interaction System with Split-Ubiquitin as Sensor," Chembiochem, 2006, vol. 7, pp. 936-942.
Extended European Search Report for European Application No. 19861495.0, mailed on Apr. 11, 2023, 8 pages.
First Office Action and Search Report for Chinese Patent Application No. 201980069124.6, dated Oct. 31, 2023, 20 pages.
Kock C., et al., "Up Against the Wall: Is Yeast Cell Wall Integrity Ensured by Mechanosensing in Plasma Membrane Microdomains?," Applied and Environmental Microbiology, Feb. 2015, vol. 81, No. 3, pp. 806-811.
Kondo A., et al., "Yeast Cell-Surface Display—Applications of Molecular Display," Applied Microbiology and Biotechnology, 2004, vol. 64, pp. 28-40.
Office Action for European Patent Application No. 19861495.0, mailed May 2, 2023, 10 Pages.
Office Action for Japanese Patent Application No. 2021-540780, mailed on Nov. 7, 2023, 12 Pages.
Search Report and Written Opinion for Singapore Patent Application No. SG11202102833T, mailed on Nov. 7, 2022, 13 pages.
Stovicek V., et al., "CRISPR/Cas System for Yeast Genome Engineering: Advances and Applications," FEMS Yeast Research, May 15, 2017, vol. 17, No. 5, pp. 1-16.
Wang T., et al., "The Establishment of *Saccharomyces boulardii* Surface Display System Using a Single Expression Vector," Fungal Genetics and Biology, Dec. 2, 2013, vol. 64, pp. 1-10, XP028611136.

* cited by examiner a. From upstream to downstream of ISIn
b. From TDH3 promoter to Flo428
c. From TDH3 promoter to downstream of ISIn
d. From upstream of ISIn to Flo428

(PRIOR ART)

FIG. 11A-FIG. 11B
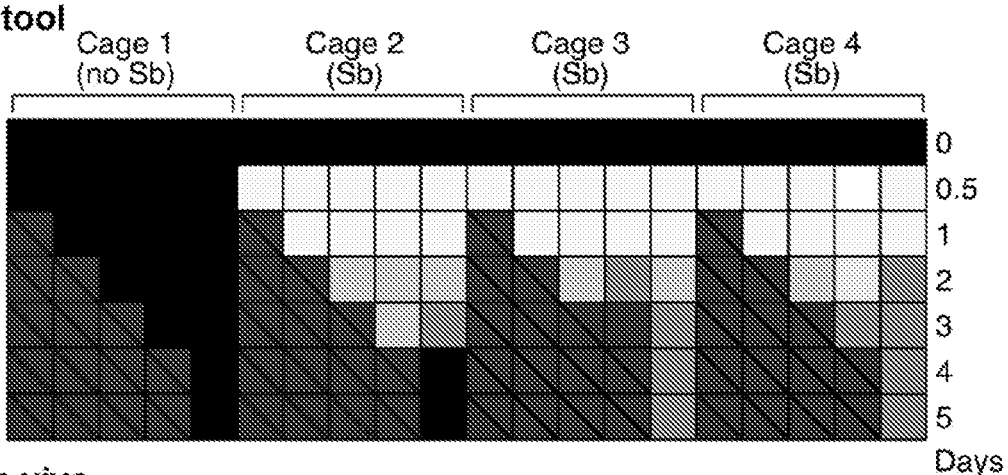
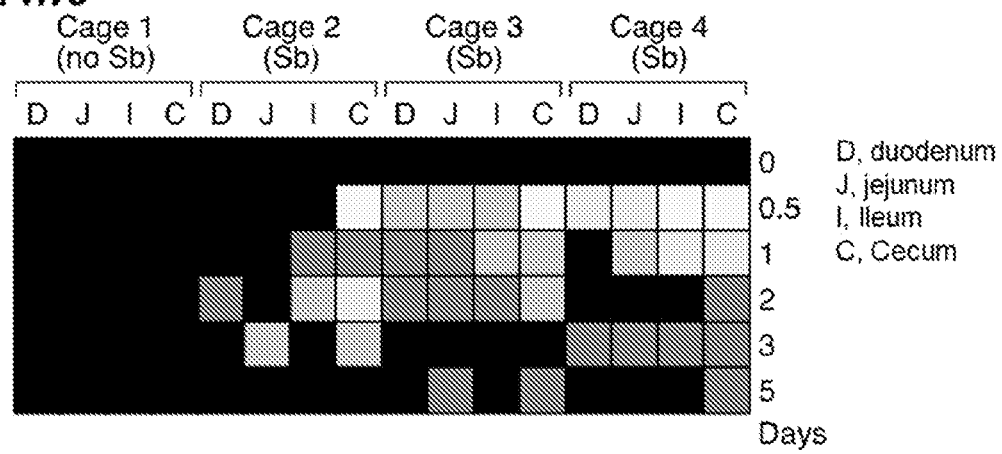
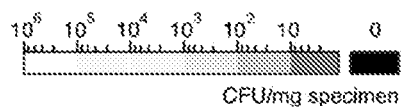

ENGINEERED MICROORGANISMS AND METHODS OF MAKING AND USING SAME

CROSS-REFERENCE TO RELATED APPLICATIONS

This application claims priority from PCT International Application No. PCT/US19/52044 filed 20 Sep. 2019, which claims the benefit of U.S. Provisional Application Ser. No. 62/733,896 filed on 20 Sep. 2018, each of which is incorporated herein by reference in its entirety.

STATEMENT REGARDING FEDERALLY SPONSORED RESEARCH OR DEVELOPMENT

This invention was made with government support under NS083698 and NS103550 awarded by the National Institutes of Health and W81XWH-18-1-0627 awarded by the Army Medical Research and Materiel Command (ARMY/MRMC). The government has certain rights in the invention.

REFERENCE TO A SEQUENCE LISTING

This application contains a Sequence Listing that has been submitted in ASCII format via Patent Center and is hereby incorporated by reference in its entirety. The ASCII copy, created Mar. 19, 2021, is named "018742-WO_PCT_Sequence_Listing_ST25.txt", and is 2443 bytes in size.

FIELD OF THE INVENTION

The present disclosure generally relates to engineered microorganisms.

SUMMARY OF THE INVENTION

Among the various aspects of the present disclosure is the provision of engineered microorganisms and methods of making and using same for use in surface display of binding agents and for sensing applications.

An aspect of the present disclosure provides for an engineered microorganism comprising: at least one binding agent displayed on a surface of the engineered microorganism, wherein the binding agent has a binding affinity to a target microorganism.

In some embodiments, the binding agent is operably linked to the engineered microorganism via an anchor protein.

In some embodiments, the anchor protein is a cell wall protein anchor region.

In some embodiments, the cell wall protein anchor region is a Flo1p anchor region.

In some embodiments, the binding agent is operably linked to the engineered microorganism via a stem comprising a transmembrane protein.

In some embodiments, the transmembrane protein is selected from Wsc1p (C8A).

In some embodiments, the stem comprises a cell wall protein domain operably linked to the transmembrane protein, wherein the cell wall protein domain is capable of extending the stem into extracellular space.

In some embodiments, the cell wall protein domain is Mid2 protein (Mid2p).

In some embodiments, the engineered microorganism comprises a first binding agent and a second binding agent, wherein the first binding agent is capable of binding to a first target microorganism and the second binding agent is capable of binding to a second target microorganism and the first binding agent is different from the second binding agent.

In some embodiments, the engineered microorganism is *Saccharomyces* yeast.

In some embodiments, the engineered microorganism is selected from *Saccharomyces cerevisiae* var. *boulardii* (*S. boulardii*).

In some embodiments, the target microorganism is a pathobiont, a commensal microorganism, or a pathogen.

In some embodiments, the target microorganism is a bacteria, a fungi, a virus, or a eukaryote.

In some embodiments, the target microorganism is selected from the group consisting of Norovirus, *Listeria monocytogenes*, *Clostridium* pathobionts, *Clostridium difficile*, *Clostridium perfringens*, *Campylobacter coli*, *Staphylococcus aureus*, methicillin-resistant *Staphylococcus aureus* (MRSA), *Streptococcus pyogenes*, *Salmonella*, *P. aeruginosa*, *E. coli*, or any other biological entity having a binding region that can be targeted by a binding agent, such as scFvs, receptors, or binding domains.

In some embodiments, the binding agent specifically binds to the target microorganism.

In some embodiments, the binding agent comprises one or more of the group consisting of: peptides, proteins, antibodies, nanobodies, single chain fragments thereof, and combinations thereof.

In some embodiments, the binding agent comprises one or more of the group consisting of: a cell wall binding domain of a target microorganism and a cell wall binding domain of an endolysin.

In some embodiments, the anchor protein comprises a cell wall protein anchor region in a single cistron bracketed by a promoter and a terminator.

In some embodiments, the target microorganism is norovirus and the binding agent is CLM-1.

In some embodiments, the target microorganism is *Clostridium* pathobionts (*C. difficile/perfringens*) and the binding agent is cell binding domain of ΦCP26F (PlyCP26F).

In some embodiments, the target microorganism is *Listeria monocytogenes* and the binding agent is cell binding domain 500 of endolysin Ply500 or cell wall binding domain of PlyP35.

In some embodiments, the target microorganism is *Streptococcus pyogenes* and the binding agent is PlyC binding domain of endolysin PlyC.

In some embodiments, the target microorganism is methicillin-resistant *Staphylococcus aureus* (MRSA) or *Staphylococcus aureus* and the binding agent is LysGH15B, a cell wall binding domain of endolysin LysGH15, LysSA97, or ZW88.

In some embodiments, the target microorganism is *Campylobacter coli* and the binding agent is a cell wall binding domain of phiCcoIBB35.

In some embodiments, the engineered microorganism comprises a transactivator operably linked to a transmembrane protein via a conditionally cleavable peptide.

In some embodiments, the conditionally cleavable peptide is cleavable in the presence of ubiquitinase.

In some embodiments, the transactivator comprises an RNA-guided DNA endonuclease enzyme.

In some embodiments, the RNA-guided DNA endonuclease enzyme is nuclease-null Cas9 (dCas9).

In some embodiments, the RNA-guided DNA endonuclease enzyme corresponds to a display unit integrated into an intergenic site.

In some embodiments, the engineered microorganism is *S. boulardii* and the intergenic site is selected from Chr VII, XII, XV, XVI, or combinations thereof.

In some embodiments, a first split ubiquitin fragment is operably linked to transmembrane protein; a transactivator is operably to the transmembrane protein via a second split ubiquitin fragment; and physical interaction between the first split ubiquitin fragment and the second split ubiquitin fragment releases the transactivator.

In some embodiments, the first split ubiquitin fragment comprises a N-terminal 37 amino acid residues of ubiquitin is operably linked to transmembrane protein; and the second split ubiquitin fragment comprises a C-terminal 42 amino acid residues of ubiquitin.

In some embodiments, the transactivator comprises a scRNA-binding motif and a transcription activator capable of initiating expression of a reporter protein.

In some embodiments, the reporter protein is selected from a fluorescent protein, such as GFP, RFP (e.g., mCherry), BFP, or a luminescence protein, such as luciferase.

In some embodiments, the transactivator comprises a transcriptional activation domain.

In some embodiments, the transcriptional activation domain comprises VP64.

In some embodiments, the transactivator comprises an RNA stem loop recognition domain and the RNA stem loop recognition domain is fused to an intracellular enzyme-cleavable-binding fragment.

In some embodiments, the RNA stem loop recognition domain is selected from MCP, PCP, or Com.

In some embodiments, the intracellular enzyme-cleavable-binding fragment is a ubiquitin fragment.

In some embodiments, the engineered microorganism comprises a reporter gene.

In some embodiments, the reporter gene is selected from GFP, RFP, BFP, luminescence proteins, or combinations thereof.

In some embodiments, the engineered microorganism is selected from a microorganism that does not colonize in a mammalian gut.

An aspect of the present disclosure provides for a method of targeted sensing, detecting, or killing of commensal or pathogenic gut microbes comprising administering a therapeutically effective amount of the engineered microorganism of any one of the above-mentioned engineered microorganisms.

An aspect of the present disclosure provides for method of treating a gut disease (e.g., infectious disease, such as norovirus) comprising administering a therapeutically effective amount of an engineered microorganism of any one of the above-mentioned engineered microorganisms.

An aspect of the present disclosure provides for a method of regulating commensal gut microbiota comprising contacting a therapeutically effective amount of an engineered microorganism of any one of the above-mentioned engineered microorganisms.

An aspect of the present disclosure provides for a method of constructing an engineered microorganism comprising: providing a microorganism;
providing a display cassette; and integrating the display cassette into an intergenic site of the microorganism genome; wherein the display cassette comprises a sequence for expression of a binding agent; a promoter capable of expressing the binding agent; a terminator; an anchor; and a secretion signal peptide.

In some embodiments, the anchor comprises a cell wall protein anchor region in a single cistron bracketed by a constitutive promoter and a terminator.

In some embodiments, the anchor is selected from Cwp2p, Sed1p, Ccw12p or Flo1p from *Saccharomyces* yeasts.

In some embodiments, the anchor is selected from Flo1p.

An aspect of the present disclosure provides for a method of constructing an engineered microorganism comprising: providing a microorganism; providing a display cassette; and integrating the display cassette into an intergenic site of the microorganism genome; wherein the display cassette comprises a sequence for expression of a binding agent; a constitutive promoter; a terminator; a stem comprising a transmembrane domain of a microorganism cell wall protein; a secretion signal peptide; and an intracellular enzyme-cleavable-binding fragment (e.g., fragments of ubiquitin) operably linked to a transactivator.

In some embodiments, the transmembrane domain of a microorganism cell wall protein is selected from Wsc1p (C8A).

In some embodiments, the display cassette further comprises a cell wall protein domain operably linked to the stem, wherein the cell wall protein domain is capable of extending the stem into extracellular space.

In some embodiments, the method comprises a first pair of binding agents and a second pair of binding agents; and a first transactivator and a second transactivator; wherein the first pair of binding agents are capable of binding to a first target microorganism and the second pair of binding agents are capable of binding to a second target microorganism and the first pair of binding agents are different from the second pair of binding agents; the first pair of binding agents are operably linked to a first pair of intracellular enzyme-cleavable-binding fragment (e.g., ubiquitin fragment) via a first transmembrane protein, wherein one of the first pair of the first intracellular enzyme-cleavable-binding fragment is operably linked to the first transactivator; the second binding agent is operably linked to a second pair of intracellular enzyme-cleavable-binding fragments via a second transmembrane protein, wherein one of the second pair of the second intracellular enzyme-cleavable-binding fragment is operably linked to a second transactivator; and one of the first pair of intracellular enzyme-cleavable-binding fragments and one of the second pair of intracellular enzyme-cleavable-binding fragments have the same binding protein in the N-terminal region, but have different transactivators in the C-terminal region, capable of physically interacting with target microorganisms, and releasing the first or the second transactivators.

In some embodiments, the binding agent comprises one or more of the group consisting of: peptides, proteins, antibodies, nanobodies, single chain fragments thereof, and combinations thereof.

In some embodiments, the binding agent comprises one or more of the group consisting of: a cell wall binding domain of a target microorganism and a cell wall binding domain of an endolysin.

In some embodiments, the binding agent is selected from CLM-1; ZW88; cell binding domain of ΦCP26F (PlyCP26F); cell binding domain 500 of endolysin Ply500; PlyC binding domain of endolysin PlyC; LysGH15B, a cell wall binding domain of endolysin LysGH15 or LysSA97; or cell wall binding domain of phiCcoIBB35.

In some embodiments, the transactivator is operably linked to a transmembrane protein via a conditionally cleavable peptide.

In some embodiments, the transactivator comprises an RNA-guided DNA endonuclease enzyme (e.g., nuclease-null Cas9 (dCas9)).

In some embodiments, the RNA-guided DNA endonuclease enzyme corresponds to a display unit integrated into an intergenic site (e.g., Chr VII, XII, XV, XVI for *S. boulardii*).

In some embodiments, a nuclease-null Cas9 (dCas9) and a scaffold RNA recruit the transactivator to corresponding synthetic promoters.

In some embodiments, the transactivator comprises a scRNA-binding motif and a transactivator capable of initiating the expression of a reporter (e.g., a fluorescent protein, such as GFP, RFP (e.g., mCherry), BFP, luminescence protein) or biomolecule (e.g., an antibody, enzymes, antimicrobial peptide).

In some embodiments, the transactivator comprises a transcriptional activation domain (e.g., VP64).

In some embodiments, the transactivator comprises an RNA stem loop recognition domain (e.g., MCP, PCP, Com) fused to an intracellular enzyme-cleavable-binding fragment (e.g., a ubiquitin fragment).

In some embodiments, the method comprises initiating transcription of target reporter proteins.

In some embodiments, the target reporter proteins are selected from a fluorescent protein and a luminescence protein.

In some embodiments, the target reporter proteins are selected from the group consisting of: GFP, RFP (such as mCherry), BFP, luciferase, or combinations thereof.

In some embodiments, the microorganism is selected from *S. boulardii* and the intergenic site is selected from Chr VII, XII, XV, or XVI, or a combination thereof; and corresponding guide RNAs for Cas9 yield stable expression of target proteins without interference in native transcriptions of the microorganism.

In some embodiments, frameworks for stable expression of target proteins do not require an inducer.

In some embodiments, the method comprises a strong constitutive promoter or weak promoter of the engineered microorganism.

In some embodiments, the strong constitutive promoter is selected from TDH3 or CCW12 promoters of *S. boulardii*.

In some embodiments, the weak promoters selected from WSC1 or FAU1 promoters of *S. boulardii*.

In some embodiments, the method comprises a terminator.

In some embodiments, the terminator is selected from ADH1 or CYC1 terminators of *S. boulardii*.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 11A-FIG. 11B. In vivo stability of engineered *S. boulardii* in stool (A) and in vivo (B).

DETAILED DESCRIPTION OF THE INVENTION

Figure 1:
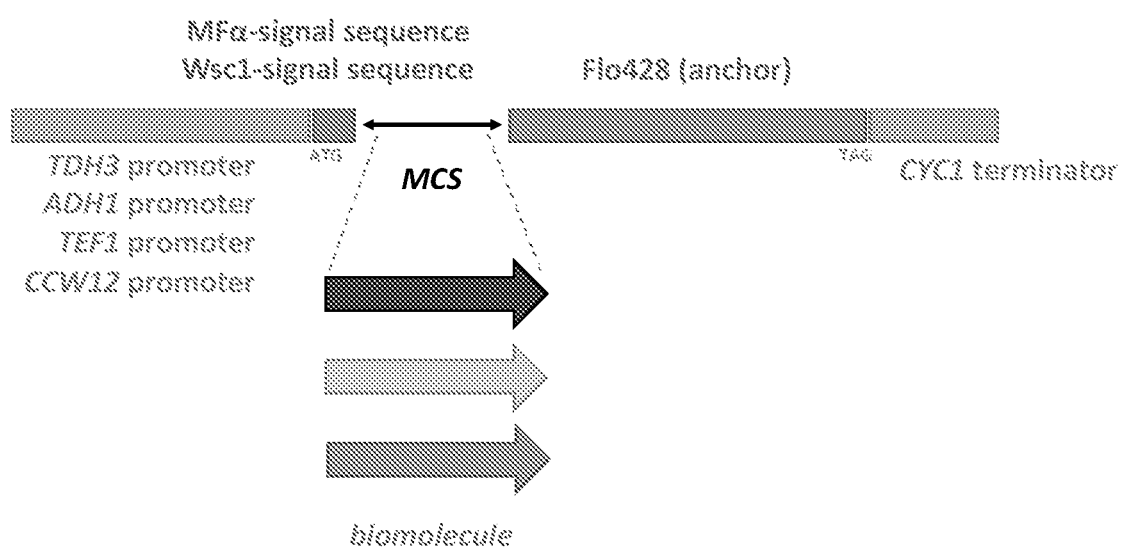
FIG. 1. A backbone cassette for yeast surface display.

The present disclosure is based, at least in part, on the discovery that an engineered *Saccharomyces boulardii* (*S. boulardii*, Sb) can be used for targeted binding, sensing, and/or killing of commensal or pathogenic gut microbes.

As described herein, the present disclosure provides for methods of engineering *S. boulardii* using biomolecules and advanced genetic toolboxes of the CRISPR system, which minimizes unfavorable extra genetic alterations and enables synthetic signaling and gene transcription mechanisms.

As described herein, the present disclosure provides for a cell surface display of biomolecules that specifically interact with or against target microorganisms, in particular, intestinal biological entities including commensal microorganisms or pathogens. Commensal and pathogenic microorganisms can be bacteria, viruses, or eukaryotes.

As described herein, the present disclosure provides for a cell surface display of biomolecules in order to manipulate binding, sensing, modulation, and destruction capabilities of a microorganism, such as a probiotic yeast, *Saccharomyces*

*cerevisiae* var. *boulardii* (*S. boulardii*), against target microorganisms (e.g., pathogens) in the host gut.

As described herein, the present disclosure provides for strategies of using engineered microorganisms, such as *S. boulardii*, in clinical applications such as antimicrobial therapy and diagnosis of the gut microbiome and virome.

The strategies for making the engineered yeast disclosed herein for *Saccharomyces* yeasts including *Saccharomyces boulardii* and *Saccharomyces cerevisiae* (both are almost identical) could be applied to other yeasts, such as *Pichia pastoris* and *Hansenula polymorpha*—although not probiotic yeasts, they are generally recognized as safe (GRAS), but are not as genetically amenable as *Saccharomyces*.

Engineered Microorganism

As described herein, microorganisms can be engineered to sense, detect, and/or treat/destroy (e.g., remove pathogen).

Engineering the microorganism with biomolecules was performed using advanced genetic toolboxes of the CRISPR system. For example, the present disclosure provides for fungal biosensors, wherein the biosensor selectively recognizes or reacts to a wide range of sensible microbial entities.

The engineered microorganism can comprise an extracellular binding agent (e.g., a peptide with a binding domain, such as scFv, cell wall binding domains of endolysins, and receptors), an extracellular anchor protein (e.g., Mid2p, ubiquitinase, Flo428), an intracellular anchor protein (e.g., Mid2p, ubiquitinase, Flo428), a transcription system (e.g., transcription factor/transactivator), or a therapeutic agent.

To accomplish the disclosed *S. boulardii* applications, novel intergenic sites at chromosome VII, XII, XV, and XVI, and corresponding guide RNAs for Cas9 were selected and designed, respectively, for stable display of target proteins (e.g., CLM-1) without interference in native transcriptions of the yeast. Frameworks for stable expression of binding agents/target proteins without the need for an inducer were constructed using inherent strong constitutive promoters (TDH3 and CCW12 promoters) or weak promoters (e.g., WSC1 and FAU1 promoter) as well as terminators (e.g., ADH1 and CYC1 terminators) of *S. boulardii*. The anchor region can be expressed together with the binding agent/binding domain as a chimeric protein.

The applications of the disclosed technology can include the "display (sponge)" design and the "sensor" design.

a. The Flo428 (C-term 428 aa residue of Flo1 protein) "anchor" protein was used for the display design. The role of Flo428 is stable and simple display of target proteins on the surface of yeasts.

b. The mutant Wcs1 was used as a "transmembrane" protein for the sensor design. The major role of mtWsc1 is to connect extracellular stimuli into intracellular signalings as a "stem." As described herein, the mtWsc1 can be elongated by adding S/T-rich region of Mid2 protein (Mid2 protein is a type of cell wall protein, similar to Flo1 protein), but not considered an anchor for the purposes of the sensor design.

Anchor Protein for Display Design

The microorganism can be engineered to incorporate anchor proteins on the membrane of the microorganism. An anchor protein can be any anchor protein suitable for anchoring a binding agent on the surface of the engineered microorganism.

An anchor protein can be a cell wall protein (see e.g., Example 1). For example, an anchor protein can be a peptide (e.g., cell wall protein carrying a serine/threonine-rich region). Examples of anchor proteins can be Cwp2p, Sed1p, Ccw12p or Flo1p of *Saccharomyces* yeasts.

For example, a Flo1 anchor (Flo428) has been used mainly in metabolic engineering area as a display tool for enzymes but was discovered to be useful for this purpose. As such, a simple single chimeric protein displaying a target protein extracellularly can be constructed using Flo428.

Moieties (e.g., sensors, binding agents) can be attached extracellularly on the surface of the microorganism or intracellularly, inside the cell via anchor proteins. For example, the anchor protein can act as a linker group to link a cell membrane and targeting, sensing, or therapeutic moieties.

As described herein, the anchor region is expressed together with the binding domain as a chimeric protein.

Stem for Sensor Design

The present disclosure provides for a stem for use in the biosensor/detector application of the engineered microorganism system.

As described herein, the yeast biosensors, do not use an "anchor" protein region. Instead of the anchor region used in the surface display design, the chimeric proteins for the sensing mechanism have a "stem" which is a transmembrane protein whose position is stretched from cytoplasm to extracellular space (see e.g., FIG. 3). Although the module protein comprises similar S/T-rich region to the anchor protein for the display design (sponge) the sensor module chimeric proteins should not be anchored.

For example, the C-terminal end of the stem can be selected from an RNA stem loop recognition domain (e.g., MCP, PCP, Com) fused to an intracellular enzyme-cleavable-binding fragment (e.g., ubiquitin fragment).

As another example, the stem can be selected from mutant Wsc1p (C8A) molecules (transmembrane proteins). Wsc1p (C8A) is a preferred stem as it cannot be clustered regardless of physical stresses. The wild type protein is self-clustering, but it was previously shown that one point mutation (C8A) can make this protein to not cluster. As such, the mutant Wsc1p was suitable for the stem moiety (see e.g., FIG. 2).

The stem can be extended by a cell wall protein domain or an elongating moiety, such as Mid2 protein (Mid2p).

Microorganism

The disclosed system uses a microorganism (e.g., fungi, yeast, bacteria, probiotic (bacteria, yeast)) to display biomolecules or binding agents.

A preferred microorganism does not colonize the gut, and is thus, easily controlled. The studies as disclosed herein, were designed considering unique characteristics and capabilities of yeasts, such as incapability of colonization, advanced posttranslational modification (compared to bacteria), and the presence of yeast transmembrane proteins. As such, the preferred microorganisms are yeasts. For example, the yeast can be a species of *Saccharomyces* (e.g., *S. boulardii*).

Due to its inability to colonize the human gut, *S. boulardii* can be engineered to act as an antimicrobial agent that absorbs or adheres to targeted microorganisms, passes through the host gut with the target microorganism bound, consequently decreases the target population and the infectious impacts of the microorganism.

As described herein, the surface display system for *S. boulardii* can be constructed by combining mating factor alpha secretion signal peptides, biomolecules that bind the target microorganisms, and cell wall protein anchor regions in a single cistron bracketed by a strong constitutive promoter and a terminator.

The microorganism can also be a bacteria. The bacteria can be *E. coli* (e.g., *E. coli* Nissle). *E. coli* can be engineered to absorb or adhere to targeted microorganisms and decrease the interaction between host and the target, but cannot decrease the target population due to capability of colonization of *E. coli*.

Binding Agents/Biomolecules

Binding agents, such as biomolecules (e.g., a peptide with a binding domain, such as scFv, receptors, cell wall binding domain, such as cell wall binding domains of endolysins, antibody or an antibody functional fragment) can be displayed on the surface of the engineered microorganism. As such, the engineered microorganism can be designed to have a binding affinity to a pathogen.

The binding agent or biomolecule can be a protein, an antibody, a single-chain variable fragment (scFv), or a nanobody. Combinations of a secretion signal peptide, a cell wall protein anchor region, and the binding agents (e.g., in a single cistron bracketed by a strong constitutive promoter and a terminator) thereof exhibiting binding or adhesive capabilities against a target microorganism.

As another example, the binding agent or biomolecule can be a cell wall binding domain of endolysin or any binding domain capable of exhibiting binding or adhesive capabilities against a target microorganism.

The binding agent can be any agent that binds to a target microorganism (e.g., pathogen, such as norovirus). For example, the binding agent can comprise a target microorganism binding domain (e.g., a virus or bacterial binding agent) (see e.g., FIG. 3). The binding agent can target, for example, pathogen or other disease, such as Norovirus, *Clostridium difficile*, *Clostridium perfringens*, *Listeria monocytogenes*, *Streptococcus pyogenes*, *Staphylococcus aureus*, including methicillin-resistant *Staphylococcus aureus* (MRSA), *P. aeruginosa*, or any other microbial entities whose binding domains are available. In a preferred embodiment, the target microorganism is a gut pathogen.

As described herein, the scFvs ZW88 was expressed in a microorganism (e.g., *S. boulardii*) that has binding affinity to *S. aureus*.

As described herein, a norovirus receptor was expressed in a microorganism (e.g., *S. boulardii*) that has binding affinity to norovirus, acting like a sponge to remove norovirus.

For example, the binding agent can be any cell wall binding domain of endolysins or cell wall binding domain for any pathogen. In some embodiments, the binding agent can be selected from any binding domain for a target microorganism. For example, the binding agent can be any one of PlyCB from endolysin PlyC (for the target microorganism *Streptococcus pyogenes*), CLM-1 (for norovirus), the cell wall binding domain (CBD) of ΦCP26F (for *Clostridium* pathobionts), CBD500 from endolysin Ply500 (for *Listeria monocytogenes*), LysSA97 (*S. aureus*), the cell wall binding domain of PlyCP26F (*C. difficile/perfringens*), the cell wall binding domain of PlyP35 (*L. monocytogenes*), the cell wall binding domain of LysGH15B of endolysin LysGH15 (for MRSA infection or a *Staphylococcus aureus* infection), the cell wall binding domain of phiCcoIBB35 (*Campylobacter coli*), or a combination thereof.

For example, the surface display of cell wall binding domain of endolysin PlyP35 exhibiting specific lytic activity against *Listeria monocytogenes*, is expected to control listeriosis with minimized undesirable interaction with commensal gut microbiota. This approach can be extended to not only regulation of other pathogenic microorganisms (e.g., *Listeria monocytogenes* and CBD500 from endolysin Ply500, *Streptococcus pyogenes* and PlyCB from endolysin PlyC) but also effective control of the shape of commensal gut microbiota (e.g., regulation of *Clostridium* pathobionts using CBD from ΦCP26F).

For a chimeric sensor, a single chain is preferred. As such, nanobodies or other antibody formats with more than one chain are not a preferred embodiment as a binding agent in the chimeric sensor design. But non-single chain nanobodies or other antibody formats can be easily incorporated into the display (sponge) design.

Target Microorganism

As described herein, the present disclosure provides for a cell surface display of biomolecules that specifically interact with or against target microorganisms, for example, intestinal biological entities such as commensal microorganisms and pathogens. Commensal and pathogenic microorganisms can be bacteria, viruses, or eukaryotes.

The engineered microorganism can be designed to bind to or target a target microorganism. The engineered microorganism can comprise a binding agent comprising a binding moiety targeting a target microorganism.

The target microorganism can be a bacteria, a fungi, a virus, or a eukaryote. The target microorganism can be a pathobiont, a pathogen, or a commensal symbiont. The target microorganism can be Norovirus, *Listeria monocytogenes*, *Clostridium* pathobionts, *Clostridium difficile*, *Clostridium perfringens*, *Campylobacter coli*, *Staphylococcus aureus*, methicillin-resistant *Staphylococcus aureus* (MRSA), *Streptococcus pyogenes*, *Salmonella*, *P. aeruginosa*, or *E. coli*.

It is presently believed that there is no limit of the range of target microorganisms that can be targeted using this method. As such, any microorganism with a specific binding domain can be targeted.

Specific binding can refer to the binding of a ligand to a receptor, and it can be possible that there is more than one specific binding site for one ligand.

Reporters for Artificial Sensors/Signaling System

The engineered microorganism can be engineered to incorporate reporters for use in artificial sensing and signaling.

The engineered microorganisms described herein can comprise a reporter (or sensor). The reporter can be a sensor protein to detect pH, an immune receptor, or reporter proteins (e.g., GFP, RFP (e.g., mCherry), BFP, luminescence protein (e.g., luciferase)).

For example, the engineered microorganism can comprise a transcription system. The transcription system can comprise a transactivator, wherein the artificial sensor can convert a physical stimulus to transcriptional signal (see e.g., FIG. 2).

Figure 3:
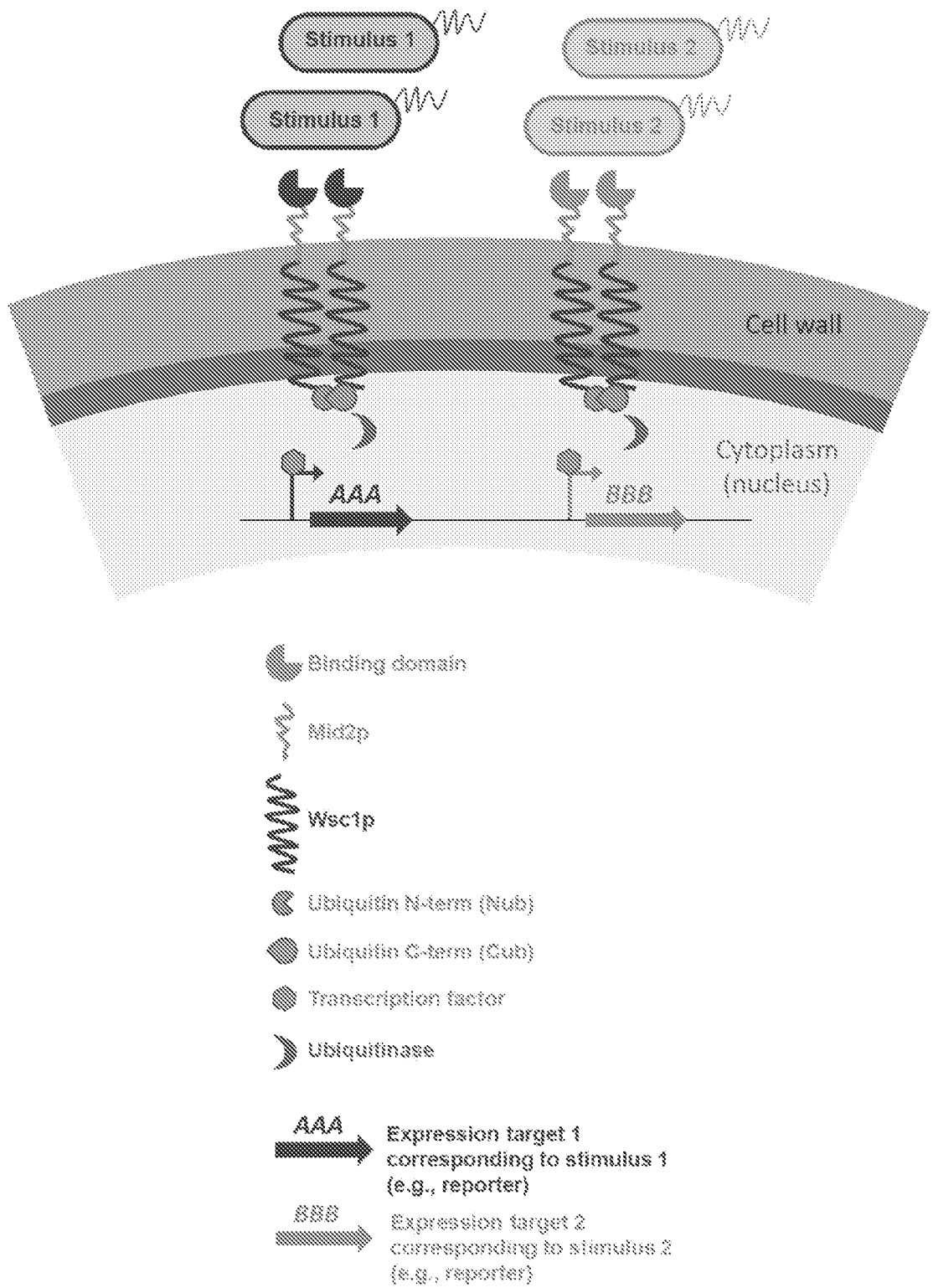
FIG. 3. Mechanism of sensing and signaling based on dCas9.
Figure 4:
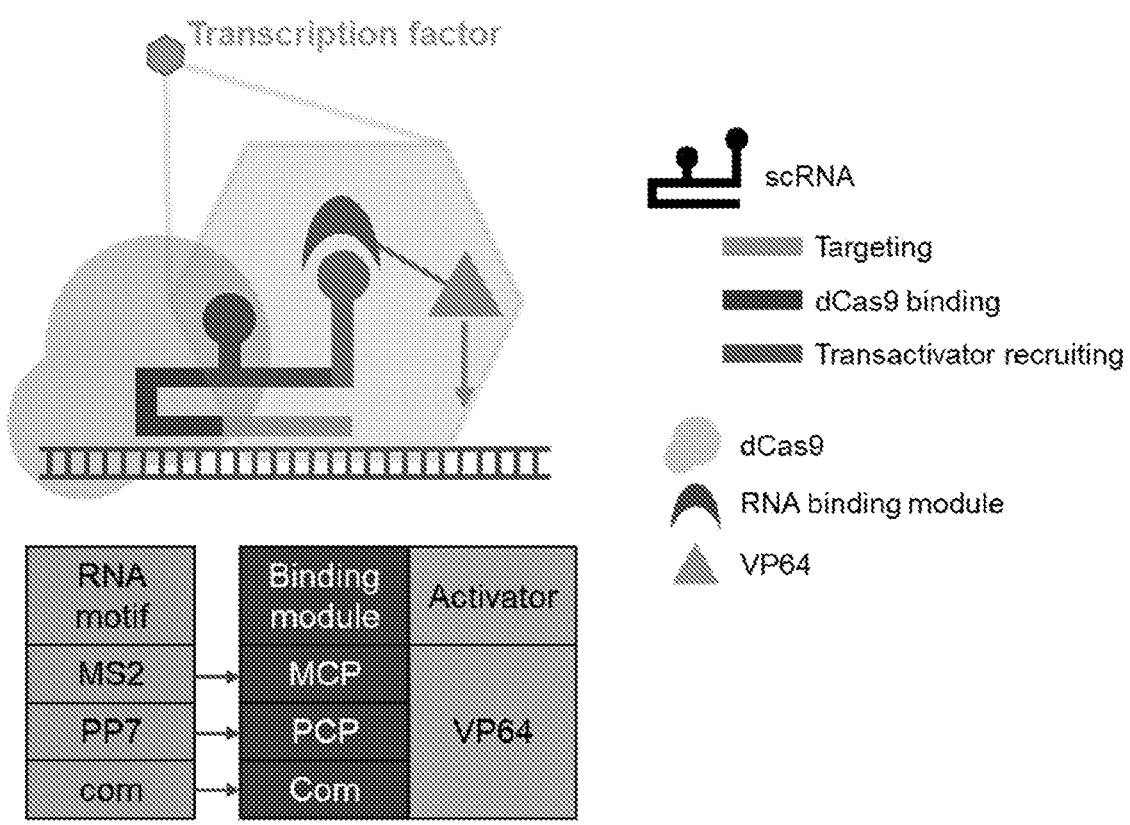
FIG. 4. Structure of artificial transactivator based on scaffold RNA.
Figure 15:
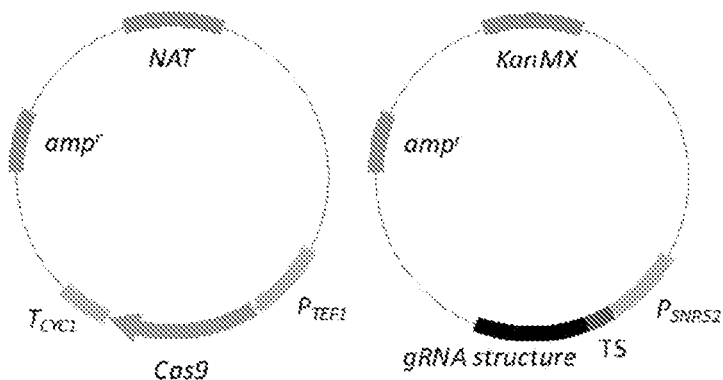
FIG. 15. CRISPR-based genome editing tools.

An artificial transactivator can be designed based on dCas9 and scaffold RNA (scRNA, see e.g., FIG. 3, FIG. 4, FIG. 15, TABLE 1). For example, a transactivator can comprise a transcriptional activation domain (e.g., VP64) and an RNA stem loop recognition domain (e.g., MCP, PCP, Com).

Pathogen Removal (e.g., Sponge)

As described herein, the present disclosure provides for novel applications of a microorganism (e.g., yeast) surface display for clinical purposes. The surface of a microorganism (e.g., a probiotic that does not colonize the human gut, such as *S. boulardii*) can be coated with a binding agent (e.g., biomolecule) that specifically binds to designated microorganisms (e.g., bacteria, fungi, viruses).

The presently described engineered microorganisms can act as a sponge to remove pathogens. For example, a microorganism capable of removing target pathogens, such as a non-colonizing yeast, can be engineered to express a pathogen receptor (e.g., norovirus receptor) on its surface to bind to the pathogen and remove it from a subject.

As such, the disclosed engineered microorganism (e.g., *S. boulardii* strains) displaying binding agents (e.g., proteins) to target microorganisms (e.g., pathogens) can be used as antimicrobial (e.g., antiviral and antibacterial agents), providing alternatives to therapeutics, such as antibiotics whose use must be tightly controlled.

Biosensors/Detectors

The present disclosure also provides for a method of constructing engineered microorganism biosensors that selectively recognize and react to a wide range of sensible target microorganisms (e.g., microbial entities) in vivo. The engineered microorganism can include a reporter.

As described herein, the engineered microorganisms can be used for sensing applications. For example, a portion of a functional protein can be attached intracellularly (e.g., via an anchor to a membrane protein) to catalyze a reaction (e.g., to turn on a transcriptional response).

Figure 17:
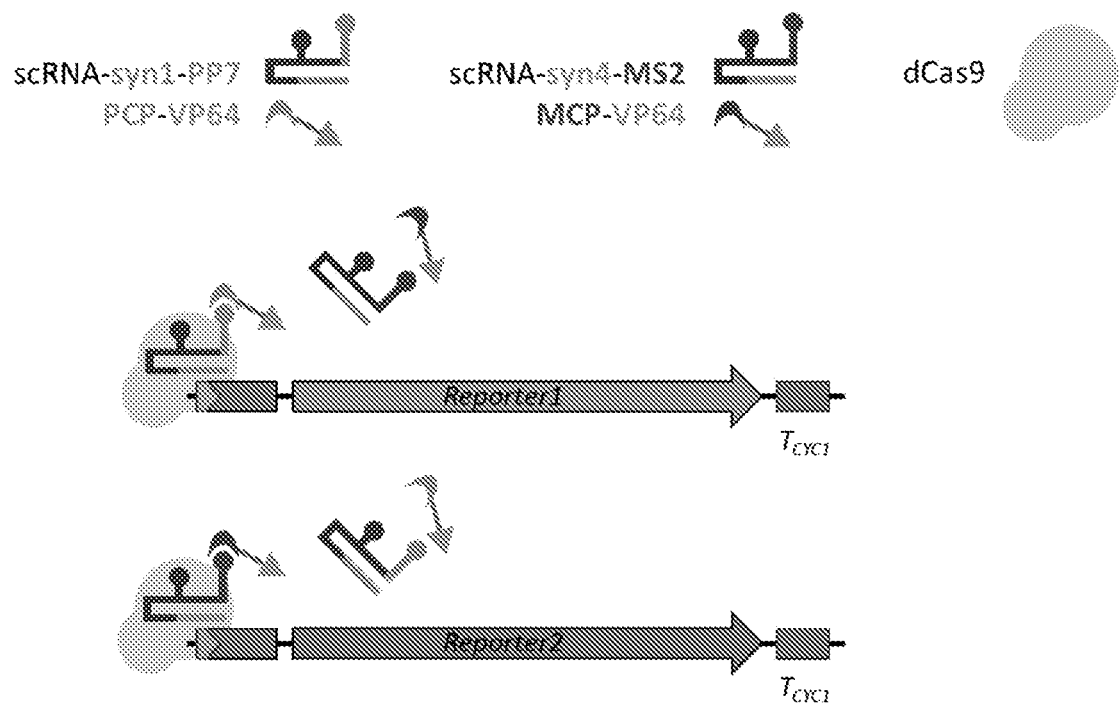
FIG. 17. Integration of reporter cassettes into genome (IS2).
Figure 20:
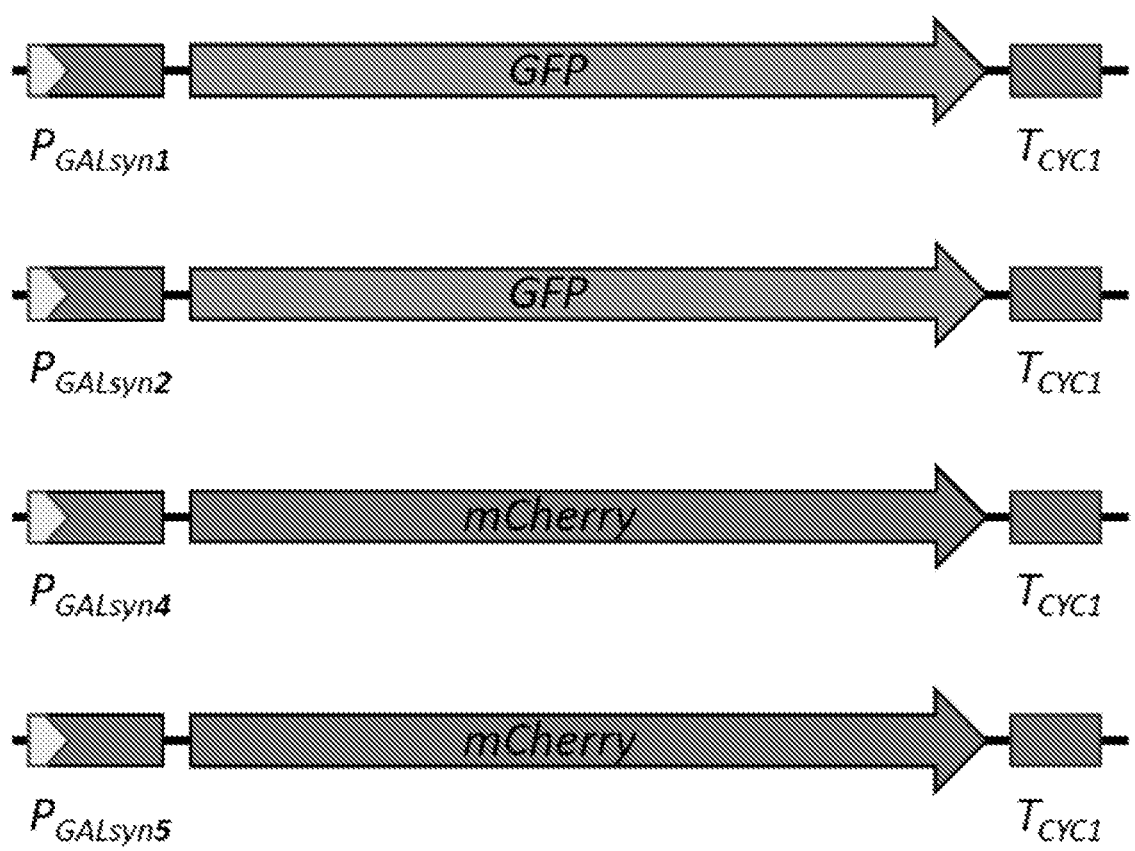
FIG. 20. Construction of new reporter cassettes.
Figure 21:
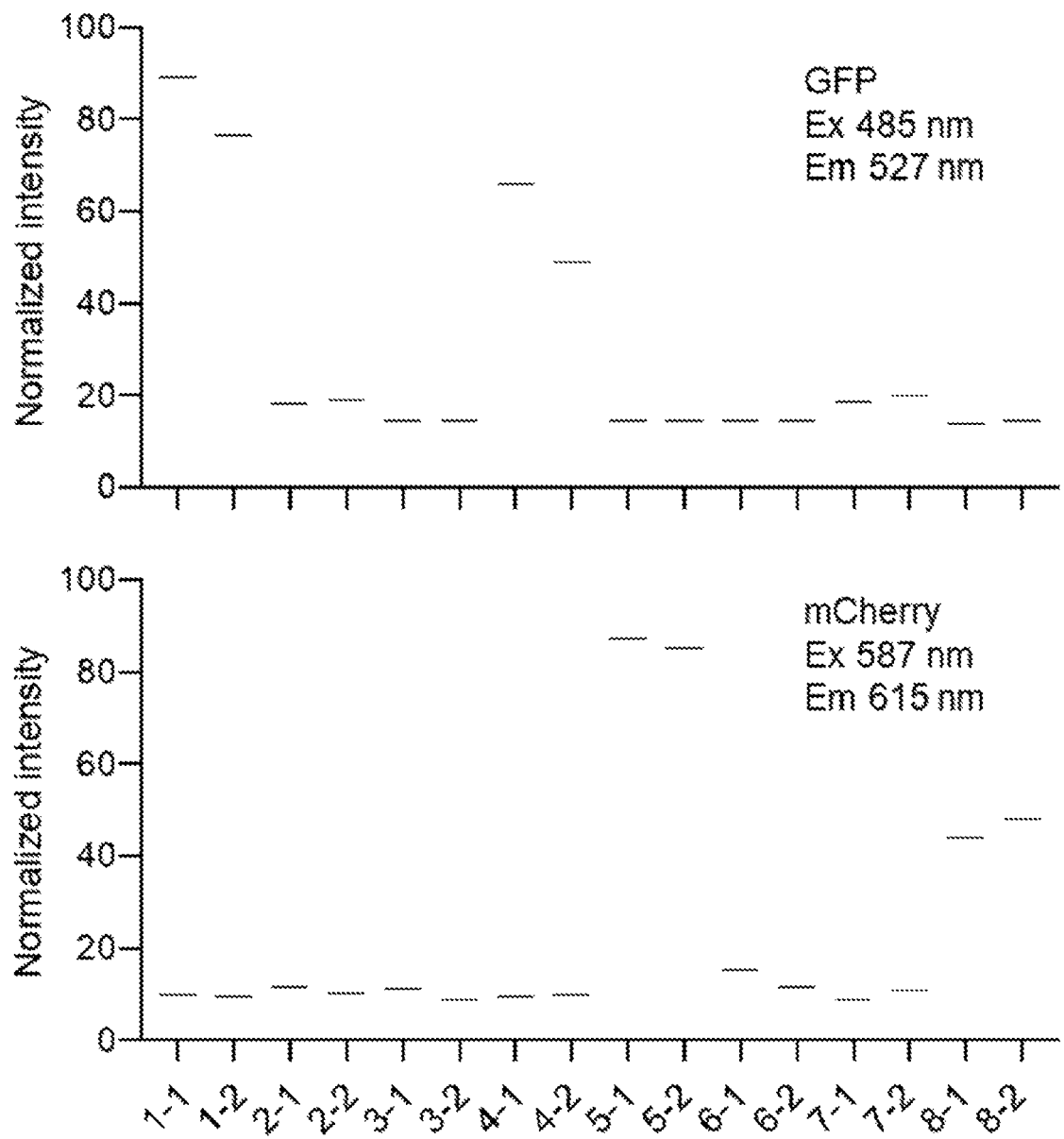
FIG. 21. Orthogonal induction of synthetic promoters by corresponding scRNAs and transactivators (see e.g., TABLE 1).

Also described herein, are engineered microorganisms that can be used for detecting (see e.g., FIG. 17, FIG. 20). For example, a transactivator can be attached to the promoter region of a detection moiety (e.g., GFP, RFP, BFP, luminescence protein). As such, every engineered microorganism that sensed a pathogen (e.g., norovirus) will light up.

Also described herein, are chimeric sensor molecules (see e.g., FIG. 3) allowing *S. boulardii* to recognize and react against a selected microorganism (e.g., microbe, bacteria, virus) constructed by combining a secretion signal peptide, a binding protein against a target microorganism, transmembrane domains of *S. boulardii* cell wall proteins, and a mutant N-terminal piece of ubiquitin or a C-terminal ubiquitin piece fused into a transactivator (expressing a transcription factor that binds to specific promoter region). Two chimeric sensor molecules with the same binding protein in the N-terminal region but different ubiquitin domains in the C-terminal region work together as a set, physically interact with the target entity (e.g., target microorganism), and release a transactivator. The nuclease-null Cas9 (dCas9) and a scaffold RNA recruit the transactivator to corresponding synthetic promoters; accordingly, the transcription of target genes, such as reporter proteins, such as RFP and GFP, can be initiated (see e.g., FIG. 3). Due to its expandability, the chimeric sensor-displaying *S. boulardii* provided herein has a much wider range of detectable microorganisms than conventional biosensors adopting bacterial or fungal sensing mechanisms.

In some embodiments, only the C-terminal ubiquitin will have a selected transactivator and the N-terminal ubiquitin is operably linked to the stem without a transactivator.

As a microbial biosensor targeting gut health, the disclosed engineered *S. boulardii* can overcome limitations of conventional approaches that depend on very limited existing sensing mechanisms in nature.

Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10:0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10:0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position +1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A constructs of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5 (9), 680-688; Sanger et al. (1991) Gene 97 (1), 119-123; Ghadessy et al. (2001) Proc Natl Acad Sci USA 98 (8) 4552-4557. Thus, one skilled in the art could generate a large number of nucleotide and/or polypeptide variants having, for example, at least 95-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. For example, amino acids with similar properties can be Aliphatic amino acids (e.g., Glycine, Alanine, Valine, Leucine, Isoleucine); Hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic and their Amide (e.g., Aspartate, Glutamate, Asparagine, Glutamine). Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m = 81.5°$ C.$+16.6$ (log $_{10}[Na^+]$)$+0.41$ (fraction G/C content)$-0.63$ (% formamide)$-(600/l)$. Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10:0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10:0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

| Conservative Substitutions I | |
|---|---|
| Side Chain Characteristic | Amino Acid |
| Aliphatic Non-polar | G A P I L V |
| Polar-uncharged | C S T M N Q |
| Polar-charged | D E K R |
| Aromatic | H F W Y |
| Other | N Q D E |

| Conservative Substitutions II | |
|---|---|
| Side Chain Characteristic | Amino Acid |
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

| Conservative Substitutions III | |
|---|---|
| Original Residue | Exemplary Substitution |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |

-continued

| Conservative Substitutions III | |
|---|---|
| Original Residue | Exemplary Substitution |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr, Phe |
| Tyr (Y) | Trp, Phe, Tur, Ser |
| Val (V) | Ile, Leu, Met, Phe, Ala |

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to overexpress. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41 (1), 207-234; Gellissen, ed. (2005) Production of Recombinant Proteins: Novel Microbial and Eukaryotic Expression Systems, Wiley-VCH, ISBN-10:3527310363; Baneyx (2004) Protein Expression Technologies, Taylor & Francis, ISBN-10:0954523253).

Methods of down-regulation or silencing genes are known in the art. For example, expressed protein activity can be down-regulated or eliminated using antisense oligonucleotides, protein aptamers, nucleotide aptamers, and RNA interference (RNAi) (e.g., small interfering RNAs (siRNA), short hairpin RNA (shRNA), and micro RNAs (miRNA) (see e.g., Fanning and Symonds (2006) Handb Exp Pharmacol. 173, 289-303G, describing hammerhead ribozymes and small hairpin RNA; Helene, C., et al. (1992) Ann. N.Y. Acad. Sci. 660, 27-36; Maher (1992) Bioassays 14 (12): 807-15, describing targeting deoxyribonucleotide sequences; Lee et al. (2006) Curr Opin Chem Biol. 10, 1-8, describing aptamers; Reynolds et al. (2004) Nature Biotechnology 22 (3), 326-330, describing RNAi; Pushparaj and Melendez (2006) Clinical and Experimental Pharmacology and Physiology 33 (5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TX; Sigma Aldrich, MO; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinformatics & Research Computing). Traits influential in defining optimal siRNA sequences include G/C content at the termini of the siRNAs, $T_m$ of specific internal domains of the siRNA, siRNA length, position of the target sequence within the CDS (coding region), and nucleotide content of the 3' overhangs.

Genome Editing

As described herein, surface displays can be performed using genome editing. Processes for genome editing are well known; see e.g. Aldi 2018 Nature Communications 9 (1911). Except as otherwise noted herein, therefore, the process of the present disclosure can be carried out in accordance with such processes.

For example, genome editing can comprise CRISPR/Cas9, CRISPR-Cpf1, TALEN, or ZNFs.

As an example, clustered regularly interspaced short palindromic repeats (CRISPR)/CRISPR-associated (Cas) systems are a newer class of genome-editing tools that target desired genomic sites in mammalian cells. Recently published type II CRISPR/Cas systems use Cas9 nuclease that is targeted to a genomic site by complexing with a synthetic guide RNA that hybridizes to a 20-nucleotide DNA sequence and immediately preceding an NGG motif recognized by Cas9 (thus, a (N) 20NGG target DNA sequence). This results in a double-strand break three nucleotides upstream of the NGG motif. The double strand break instigates either non-homologous end-joining, which is error-prone and conducive to frameshift mutations that knock out gene alleles, or homology-directed repair, which can be exploited with the use of an exogenously introduced double-strand or single-strand DNA repair template to knock in or correct a mutation in the genome. Thus, genomic editing, for example, using CRISPR/Cas systems could be useful tools for therapeutic applications targeting or sensing target microorganisms, such as pathogens.

For example, the methods as described herein can comprise a method for altering a target polynucleotide sequence in a cell comprising contacting the polynucleotide sequence with a clustered regularly interspaced short palindromic repeats-associated (Cas) protein.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intratumoral, intranasal, inhalation (e.g., in an aerosol), implanted, intramuscular, intraperitoneal, intravenous, subcutaneous, intranasal, epidural, ophthalmic, transdermal, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating a disease or microorganism infection (e.g., a viral infection, pathobiont, pathogenic microorganism infection) in a subject in need administration of a therapeutically effective amount of an engineered microorganism, so as to treat or prevent a microorganism/microbial infection.

Methods described herein are generally performed on a subject in need thereof. A subject in need of the therapeutic methods described herein can be a subject having, diagnosed with, suspected of having, or at risk for developing a microorganism infection. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and humans. For example, the subject can be a human subject.

Generally, a safe and effective amount of an engineered microorganism is, for example, that amount that would cause the desired therapeutic effect in a subject while minimizing undesired side effects. In various embodiments, an effective amount of an engineered microorganism described herein can substantially inhibit a microorganism/microbial infection, slow the progress of a microorganism/microbial infection, or limit the development of a microorganism/microbial infection.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of an engineered microorganism can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to treat or prevent a microorganism/microbial infection.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of an engineered microorganism can occur as a single event or over a time course of treatment. For example, an engineered microorganism can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for a microorganism/microbial infection.

An engineered microorganism can be administered simultaneously or sequentially with another agent, such as an antibiotic, an anti-inflammatory, or another agent. For example, an engineered microorganism can be administered simultaneously with another agent, such as an antibiotic or an anti-inflammatory. Simultaneous administration can occur through administration of separate compositions, each containing one or more of an engineered microorganism, an antibiotic, an anti-inflammatory, or another agent. Simultaneous administration can occur through administration of one composition containing two or more of an engineered microorganism, an antibiotic, an anti-inflammatory, or another agent. An engineered microorganism can be administered sequentially with an antibiotic, an anti-inflammatory, or another agent. For example, an engineered microorganism can be administered before or after administration of an antibiotic, an anti-inflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10:0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10:0879697717; Ausubel et al. (2002) Short Protocols in Molecular Biology, 5th ed., Current Protocols, ISBN-10:0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41 (1), 207-234; Gellissen, ed. (2005) Production of Recombinant Proteins: Novel Microbial and Eukaryotic Expression Systems, Wiley-VCH, ISBN-10:3527310363; Baneyx (2004) Protein Expression Technologies, Taylor & Francis, ISBN-10:0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Probiotic Yeast Engineering-Surface Display

The following example describes probiotic yeast (e.g., *Saccharomyces Boulardii*) engineering. These engineered probiotic yeast can be used in pathogen removal. This example describes the design of the construction of a surface display of antibody/binding domain and the CRISPR-based genome editing tools preparation.
Surface Display of Binding Domain Here is shown the completion of the protein display system for *S. boulardii*. The display system was constructed based on Flo428 anchor protein and was validated. The surface display did not change the stability/longevity of engineered *S. boulardii* strains in the host gut. The surface display of MNOV-binding domain enhanced in vitro binding activity of *S. boulardii* toward MNOV (~3-fold).

In vivo testing of MNOV-binding activity of engineered *S. boulardii* was performed.

Figure 9:
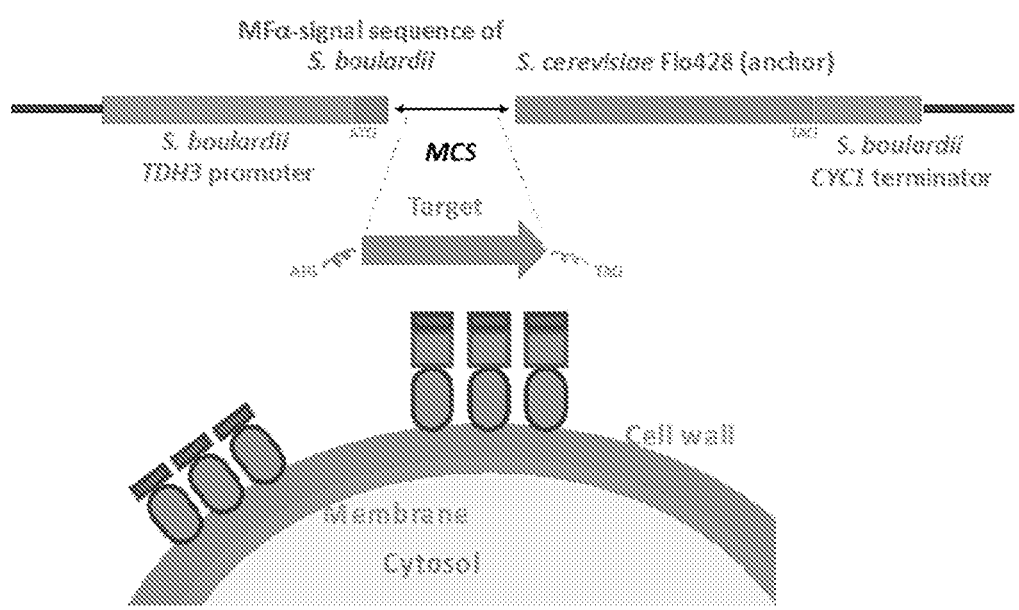
FIG. 9. Expression cassette of single chimeric protein for displaying one target peptide.
Figure 10:
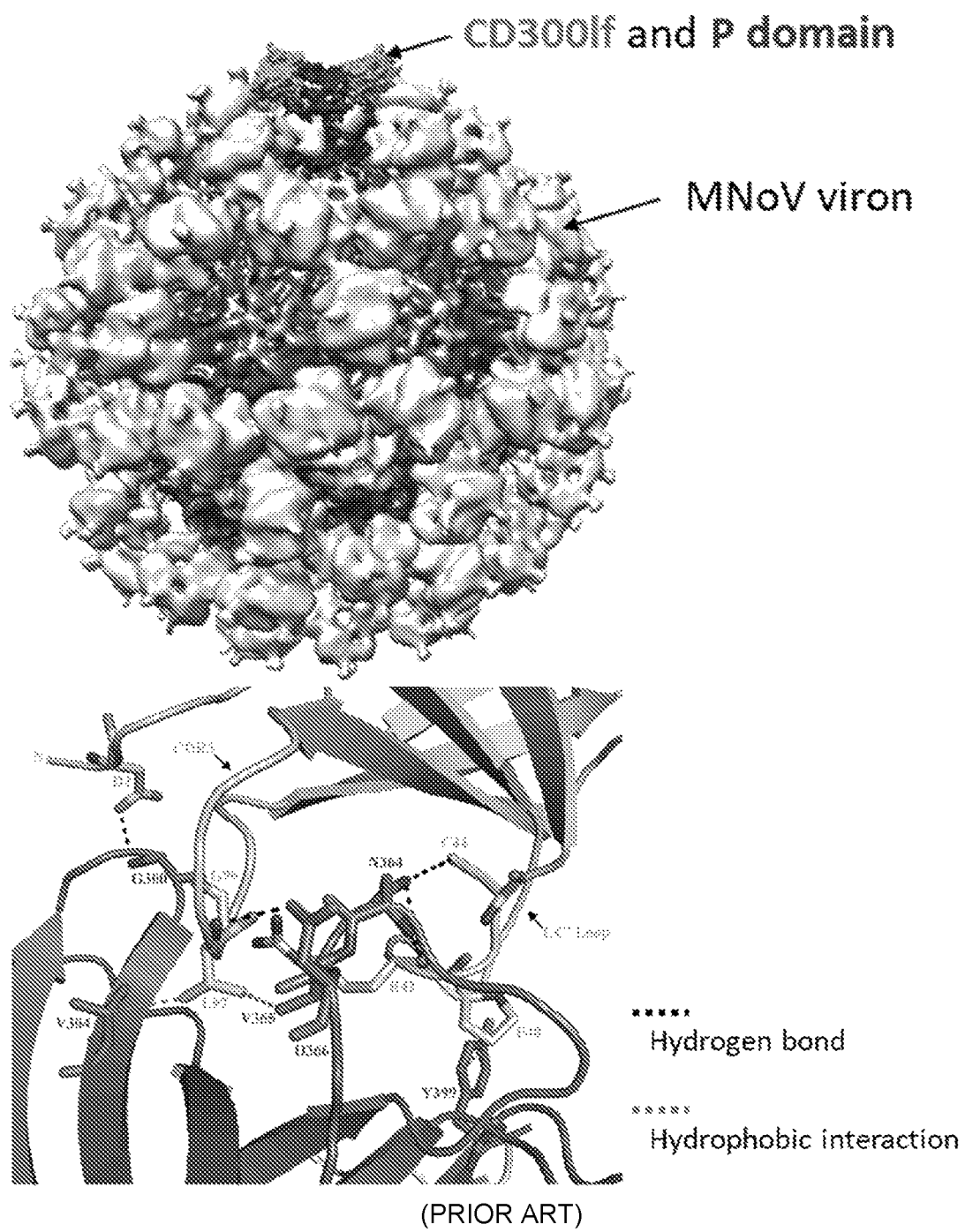
FIG. 10. Murine Norovirus (MNOV) (figure adapted from J Virol. 2018 May 14; 92 (11) Atomic Structure of the Murine Norovirus Protruding Domain and Soluble CD300lf Receptor Complex).

Displays for other pathogen-binding domains, as described here, can be made in the same manner as described herein.
Construction of Surface Display System for *S. boulardii*:

Here, the flocculin system was used. A simple cassette of single chimeric protein for displaying one target peptide (e.g., CLM-1) was constructed (see e.g., FIG. 9).

A TDH3 (Glyceraldehyde 3-phosphate dehydrogenase 3) promoter was used, demonstrating constitutive strong expression of target protein.

Mating factor α signal sequence and Flo428 (C-term 428 aa anchor region) were used for the localization of a target protein.

A CYC1 (Cytochrome C1) terminator was used.

Except for Flo428, all elements were cloned from *S. boulardii* genomic DNA.
Summary As demonstrated here, CRISPR genome editing tools, including gRNAs were successfully used to target efficient intergenic sites in *S. boulardii* genome, and a synthetic transcription system was developed based on dCas9.

Example 2: Probiotic Yeast Engineering-Yeast Biosensors

The following example describes protein displays on *S. boulardii* surface for use as fungal biosensors. This example describes the design of the construction of artificial sensors and signaling system and the CRISPR-based genome editing tools preparation.

Here, the yeast biosensors, do not use an "anchor" protein region. Instead of the anchor region used in the surface display, the chimeric proteins for the sensing mechanism have "stem" which is a transmembrane protein whose position is stretched from cytoplasm to extracellular space (see e.g., FIG. 3).

Here, a protein display on *S. boulardii* surface is shown, including cloning of the Flo1p-based surface display cassettes with a multiple cloning site to test various binding proteins and 8 combinations of 4 constitutive promoters and 2 secretion signal sequences.

Also described herein is a fungal biosensor including construction of guide RNA expression cassettes for the described 5 intergenic sites (two on Chr XVI), construction of expression cassettes of the chimeric sensor with two multiple cloning sites for testing various combinations of binding agents (biomolecules) and transactivators, construction of expression cassettes of fluorescence proteins yeRFP and yeGFP as reporters under the control of artificial promoters, and construction of dCas9 and scaffold RNA expression cassettes.
Construction of Artificial Sensors and Signaling System The synthetic transcription system was constructed and validated. Backbones of chimeric sensors were constructed based on a native transmembrane protein. A set of chimeric sensors (total 8) was constructed for the first target, *S. aureus* (scFvs, ZW88).

The wild type transmembrane protein was knocked out and the expression cassette of a sensor molecule was introduced.

This example can be expanded for the construction of new chimeric sensors using new cell wall binding domains.

Figure 5:
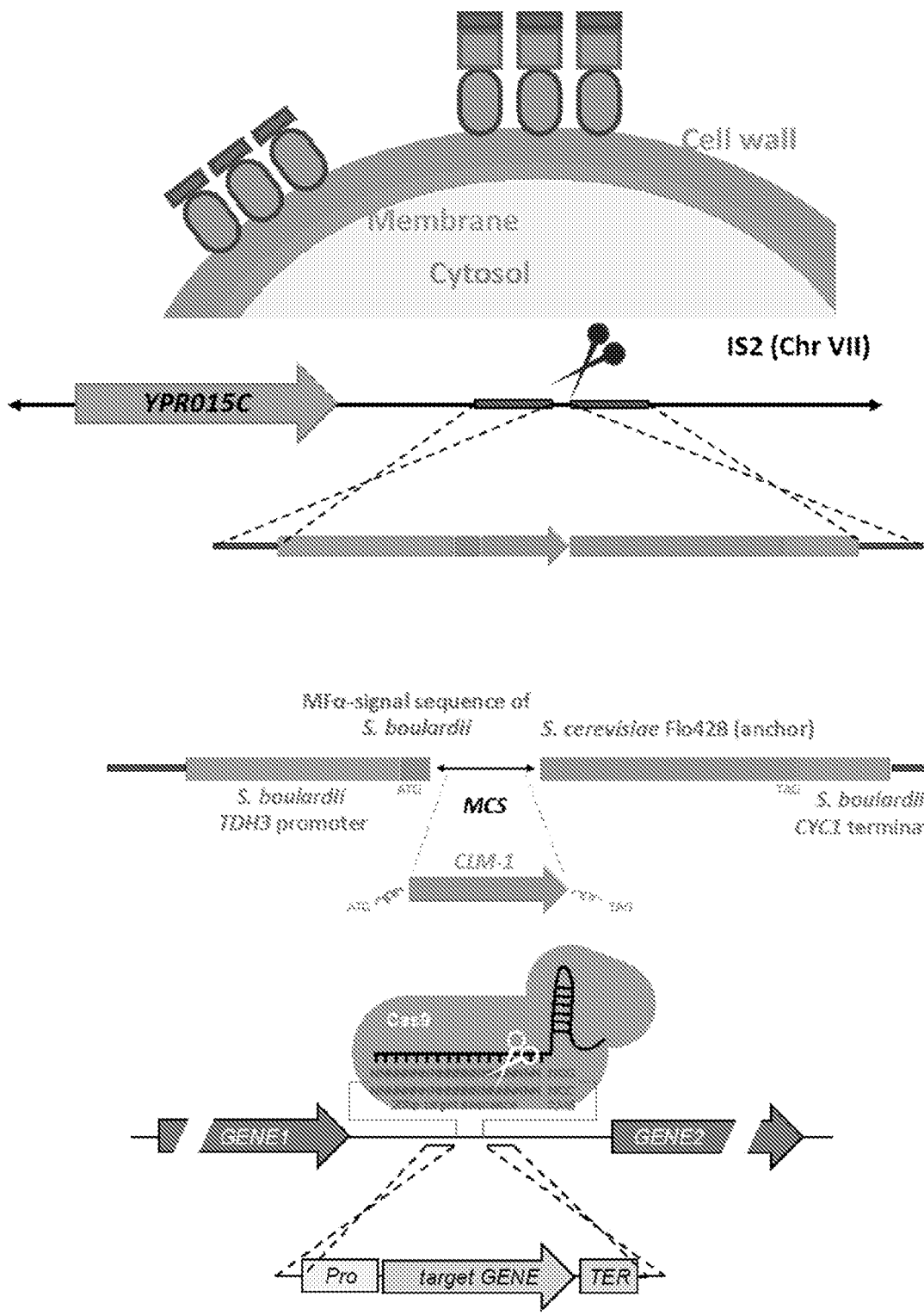
FIG. 5. Display units are integrated into safe intergenic sites (e.g., chromosome VII of *S. boulardii*) using CRISPR-Cas9.

Chimeric sensor sets were integrated into intergenic sites IS2n (for the sensor protein with N-terminal fragment of ubiquitin) and IS5n (for the sensor protein with C-terminal fragment of ubiquitin fused into transactivator) using CRISPR-Cas9 based. Coding sequences of chimeric sensor cassettes were bracketed with two homologous regions, which comprise 50 base pairs identical to the upstream and downstream of target intergenic sites IS2n and IS5n, and PCR amplified as a donor DNA for CRISPR-Cas9 genome editing. The donor DNA fragment and the expression vectors of the guide RNAs that locate Cas9 endonuclease on IS2n and IS5n, respectively, were transformed into Cas9-expressing S. boulardii (see e.g., FIG. 5). The double strand breakages on IS2n and IS5n by Cas9 were selection pressures so that it would be possible to select positive constructs that recovered from the double strand breakage by the integration of the donor DNAs via homologous recombination covering IS2n and IS5n.

Figure 2:
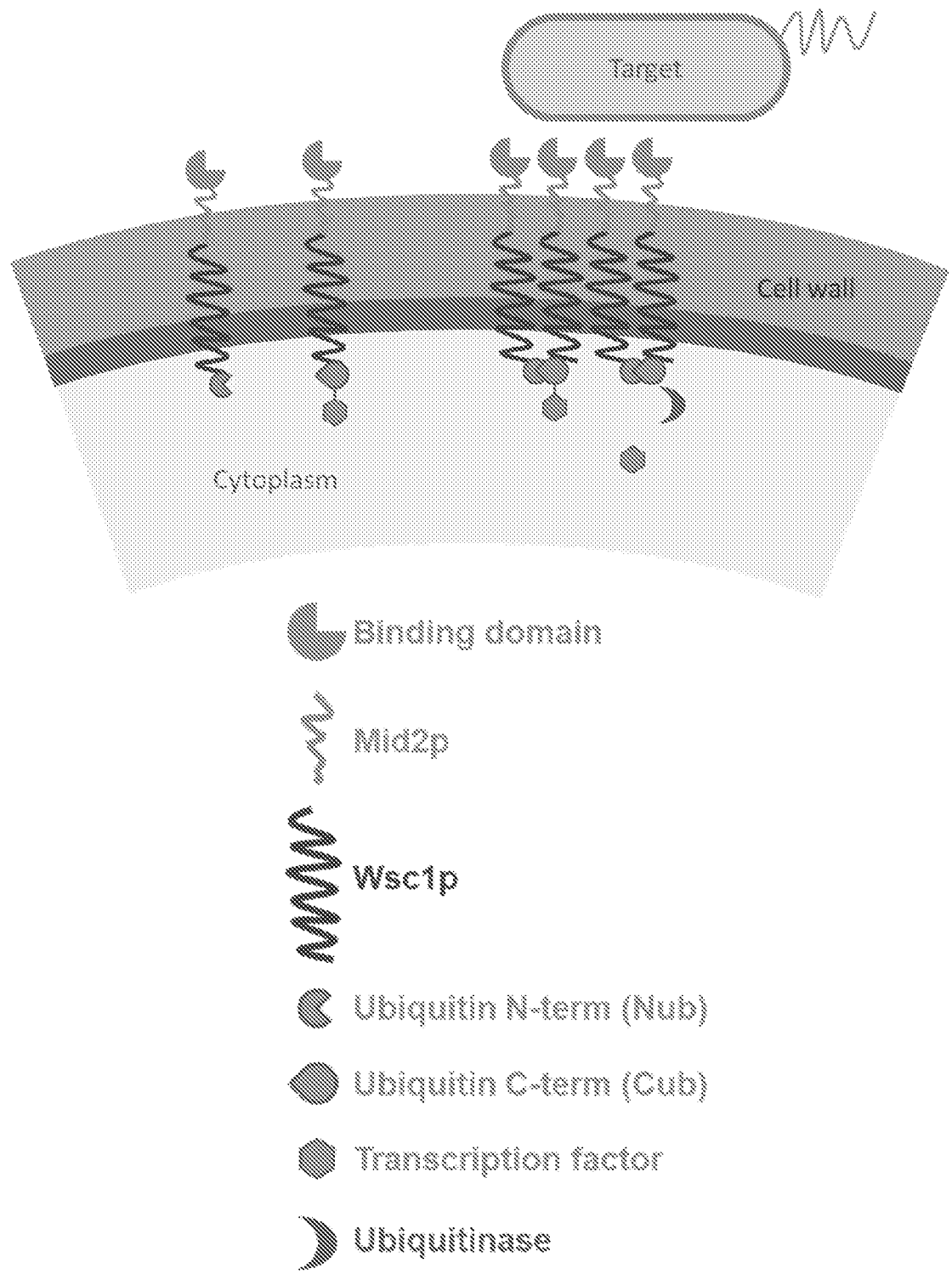
FIG. 2. Design of yeast biosensor.

Here, is shown that a chimeric sensor can convert physical stimulus to transcriptional signal (see e.g., FIG. 2). The biosensor activation is based on the innate ubiquitinase activity of Saccharomyces yeasts (see e.g., FIG. 2).

Mutant Wsc1p (C8A) molecules (transmembrane proteins) cannot be clustered regardless of physical stresses. As such, mutant Wsc1p are suitable for use as a stem moiety.

The artificial transactivator design is on dCas9 and scaffold RNA (see e.g., FIG. 3, FIG. 4).

Figure 16:
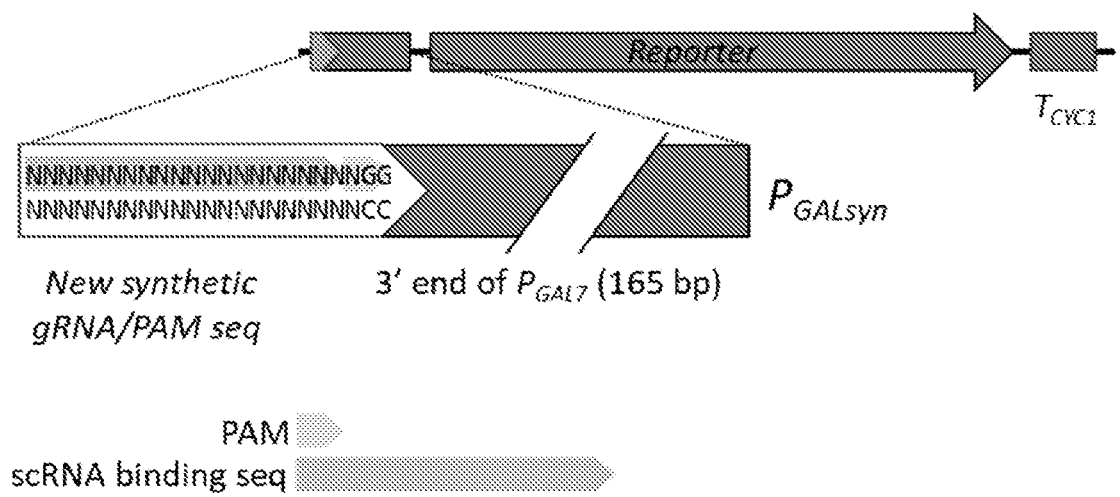
FIG. 16. For signal transmission/gene transcription.
Figure 18:
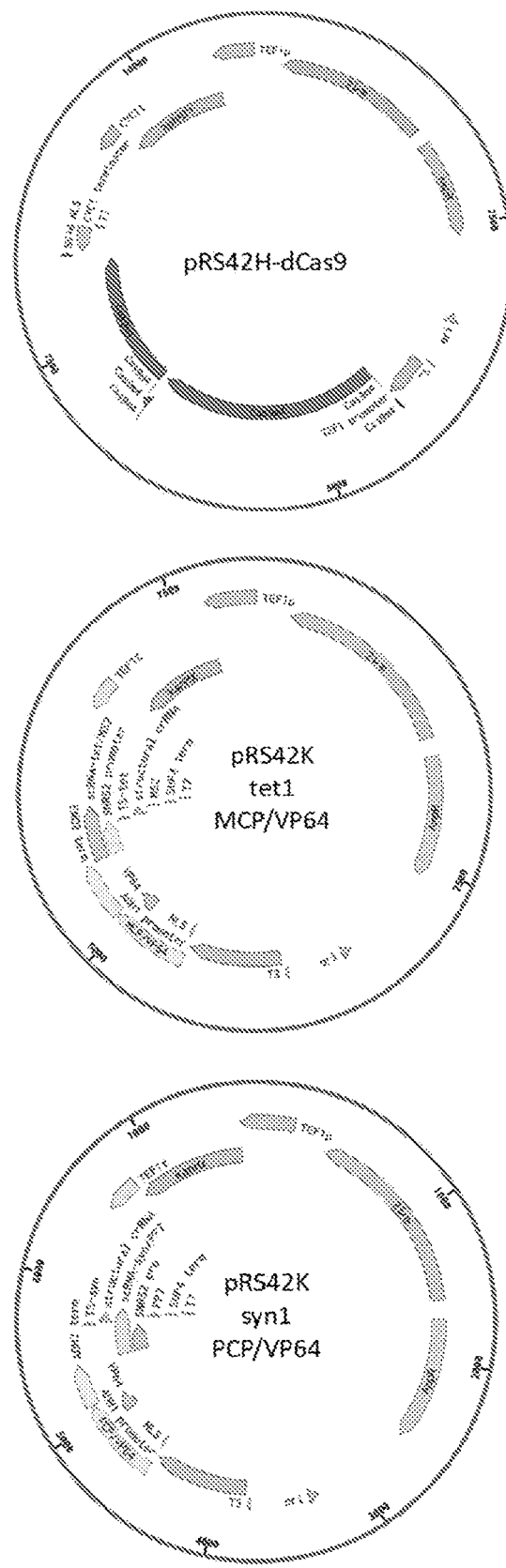
FIG. 18. Plasmids for expressing dCas9, gRNAs, and transactivators under strong constitutive promoters, $P_{TEF1}$, $P_{ADH1}$.
Figure 19:
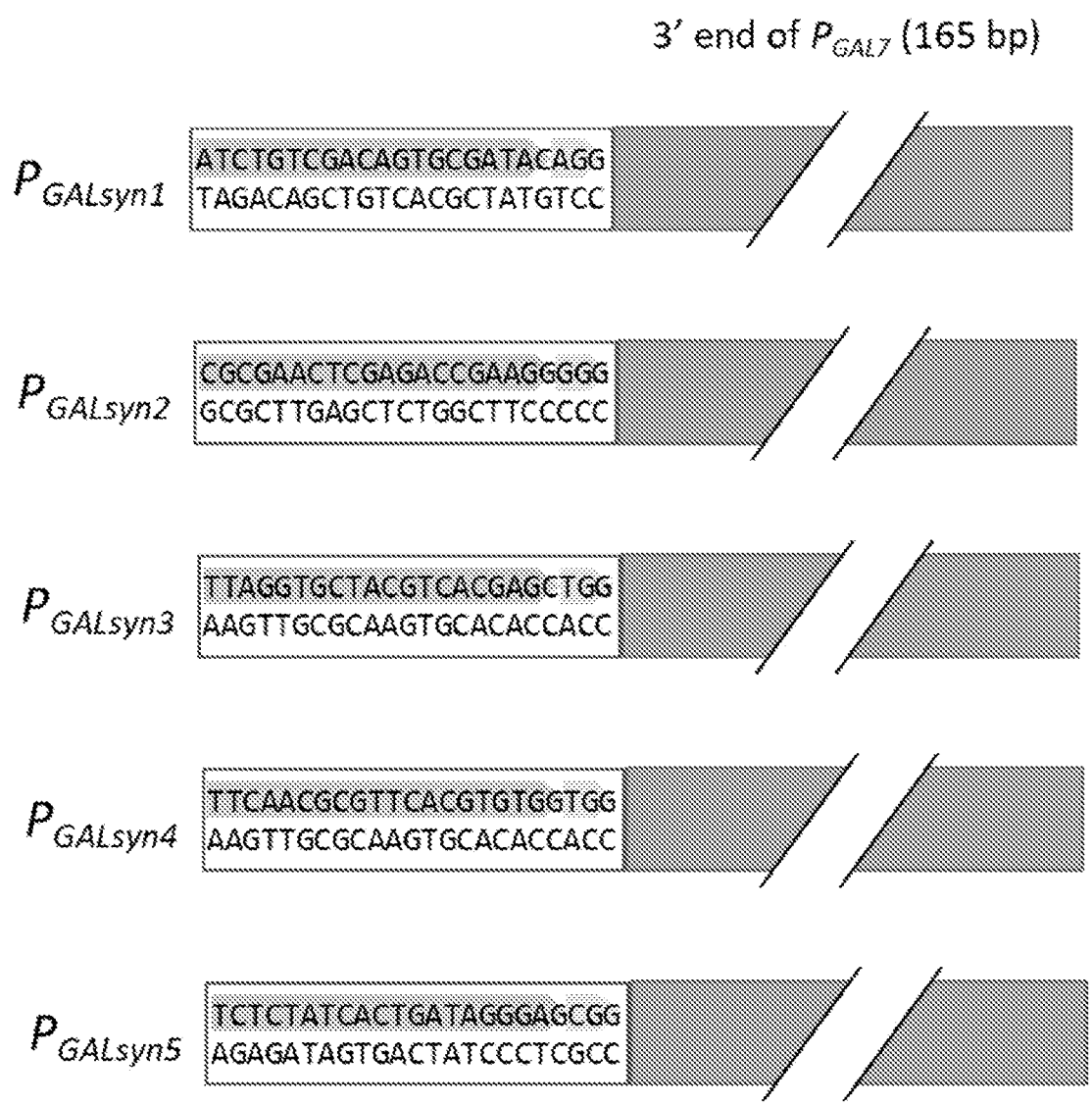
FIG. 19. New $P_{GALsyn}$ promoters and corresponding scRNAs.

Materials
  Cloning reagents: New England Biolabs
  Other chemical reagents: Sigma-Aldrich and ThermoFisher
  Oligonucleotides: Integrated DNA technologies
  S. boulardii: American Type Culture Collection
Probiotic Yeast Engineering: Chimeric Sensor
Requirements for Synthetic Biosensor in Probiotic Yeast
  The chimeric sensors have an expandable range of targets and an orthogonal expression system.
  For the sensor portion, extracellular stimuli are converted into intracellular signals.
  The binding agent can be a functional fragment of an antibody (scFv, etc.), a receptor, or a cell wall binding domain. Nanobodies or other antibody formats with more than one chain are not suitable to be adopted as the binding agent in the chimeric sensor design. But they are suitable for use in the display (e.g., sponge) design.
  Along with the sensor portion and the binding domain, the chimeric sensor comprises a transmembrane domain and a signal molecule.
  The signal transmission/gene transcription (see e.g., FIG. 15) included a promoter, a transactivator/transcription factor, and a reporter.
  CRISPR-based genome editing tools (see e.g., FIG. 16) were used for cloning. In particular, Cas9 or Cpf1 and guide RNA (gRNA).
  Test for synthetic promoter and transactivator (see e.g., FIG. 4, FIG. 17) Reporter cassettes were integrated into the genome (IS1). Episomal expression of scaffold RNA (scRNA), transactivator, and dCas9 was performed.
  Strong constitutive promoters: $P_{TEF1}$, $P_{ADH1}$ (see e.g., FIG. 18) were used.
New $P_{GALsyn}$ Promoters and Corresponding scRNAs (See e.g., FIG. 19)
  Criteria of new scRNA targeting sequences included: no self-complementarity, no same sequence in S. boulardii (cerevisiae) genome, decent efficiency, and no same sequence in other compartments of the sensor system including dCas9 expression cassette, reporter genes, and sensor expression cassette. $P_{GALsyn}1$ was designed by connecting the first scRNA binding sequence (20 base pairs) and minimal promoter region of $P_{GAL7}$ (165 base pairs from 3' end). For other promoters, the first scRNA binding sequence was substituted by other scRNA binding sequences through FastCloning method (Li et al., 2011).
Test of New P GALsyn Promoters and Corresponding scRNAs
  New reporter cassettes comprising P GALsyn promoters, reporters (GFP or RFP), and $T_{CYC1}$ were integrated into IS1n intergenic site via CRISPR-Cas9 genome editing.

TABLE 1

Strains for this experiment.

| # | Reporter cassette | | Transactivator molecules | | Expected outcome |
|---|---|---|---|---|---|
| | Promoter | Reporter | scRNA | Transactivator | |
| 1 | $P_{GALsyn1}$ | GFP | syn1-PP7 | PCP-VP64 | Green |
| 2 | $P_{GALsyn1}$ | GFP | syn2-PP7 | PCP-VP64 | No fluorescence |
| 3 | $P_{GALsyn2}$ | GFP | syn1-PP7 | PCP-VP64 | No fluorescence |
| 4 | $P_{GALsyn2}$ | GFP | syn2-PP7 | PCP-VP64 | Green |
| 5 | $P_{GALsyn4}$ | RFP | syn4-MS2 | MCP-VP64 | Red |
| 6 | $P_{GALsyn4}$ | RFP | syn5-MS2 | MCP-VP64 | No fluorescence |
| 7 | $P_{GALsyn5}$ | RFP | syn4-MS2 | MCP-VP64 | No fluorescence |
| 8 | $P_{GALsyn5}$ | RFP | syn5-MS2 | MCP-VP64 | Red |

Chimeric Sensor Converting Physical Stimulus to Transcriptional Signal (See e.g., FIG. 2).

For the sensor portion, extracellular stimuli were converted into intracellular signals: binding domain (e.g., functional antibody fragment (scFv, etc.), receptor, endolysin cell wall binding domain, etc.), a transmembrane domain, and a signal molecule.

For the chimeric sensor portion, physical stimulus is converted into transcriptional signal based on innate ubiquitinase activity of Saccharomyces yeasts.

Wild-type Wsc1p vs. mutant (C8A) Wsc1p. The wild type protein is self-clustering, but it was previously shown that one point mutation can make this protein to not cluster (C8A). Thus, the mutant Wsc1p was suitable for the stem (see e.g., FIG. 2).

A chimeric sensor converting physical stimulus to transcriptional signal was generated. Artificial and orthogonal expression by scRNA and dCas9 (see e.g., FIG. 3, FIG. 4) was demonstrated. Two different promoter-transcription factor sets were used (e.g., NUbI, NUbG). Many research groups have added transactivator at the dCas9 to control modulate transcription of target gene.

Figure 22:
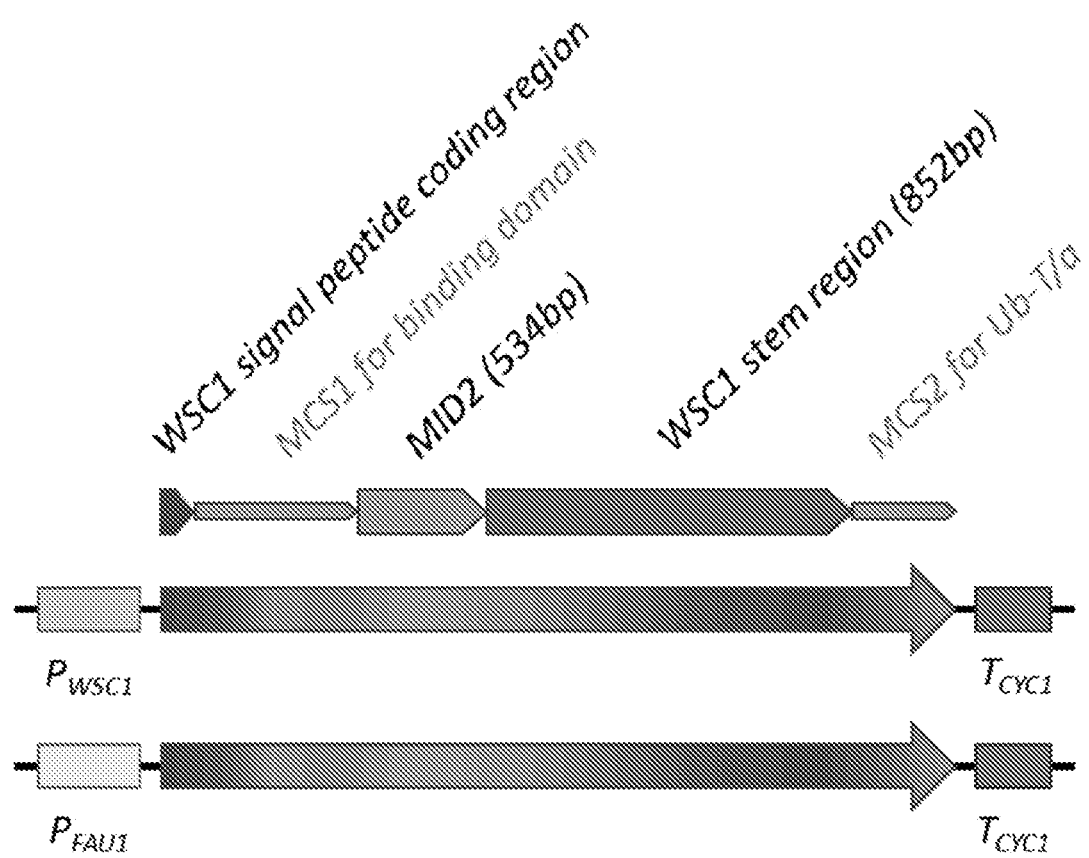
FIG. 22. A backbone cassette of chimeric sensor.

Cloning of Chimeric Sensor (See e.g., FIG. 22)

The core was constructed with a signal peptide for localization; transmembrane domains (e.g., mutant Wsc1p); MCSs for binding domain and transactivator cloning; a promoter and terminator ($P_{FAU1}$ exhibits 50% expression level of $P_{WSC1}$ in S. cerevisiae); a binding domain (ZW88 (2017, Wang et al., Appl. Microbiol. Biotechnol.), an anti S. aureus scFv.

A ubiquitin-transactivator was constructed (see e.g., FIG. 3), which included an N-term ubiquitin (NUbI or NUbG (1994, Johnsson et al., PNAS) (mutant, 113G) and a C-term ubiquitin-transactivator (CUb-MCP-VP64 or CUb-PCP-VP64). The 113G mutation of NUbG minimizes potential noise signal by the native interaction between NUb and CUb regardless of physical stimuli. The chimeric sensor was integrated into the genome.

TABLE 2

Sets prepared for testing sensor system (ZW88).

| # | Promoter | Binding domain | Wsc1p | Ub unit |
|---|---|---|---|---|
| 1 | $P_{FAU1}$ | ZW88 | mt | Cub-PCP-VP64 |
| 2 | $P_{FAU1}$ | ZW88 | wt | NUbG |
| 3 | $P_{FAU1}$ | ZW88 | mt | NUbI |
| 4 | $P_{FAU1}$ | ZW88 | mt | NUbG |
| 5 | $P_{HSC1}$ | ZW88 | mt | NUbG |
| 6 | $P_{HSC1}$ | ZW88 | mt | CUb-PCP-VP64 |

Summary

As demonstrated here, a core structure of the chimeric sensor was developed.

Example 3: Target-Murine Norovirus (MNoV)

The following example describes the use of the yeast surface display described above, targeting norovirus. It was demonstrated that the engineered *S. boulardii* displayed CLM-1.

A flocculin system was used for yeast surface display (see e.g., FIG. 1). A simple single cassette was used for displaying one target protein. A glyceraldehyde 3-phosphate dehydrogenase 3 (TDH3) promoter was used for constitutive strong expression. A mating factor α signal sequence was used for localization on a cell surface. The anchor protein used was the anchor region of Flo1p, a lectin-like cell wall protein (C-term 428 aa (1284 bp), Flo428). Cytochrome C1 (CYC1) terminator was selected for use.

Figure 6:
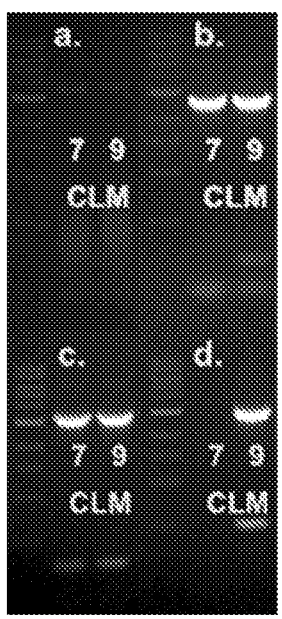
FIG. 6. Validation of chromosomal integration.
Figure 7A:
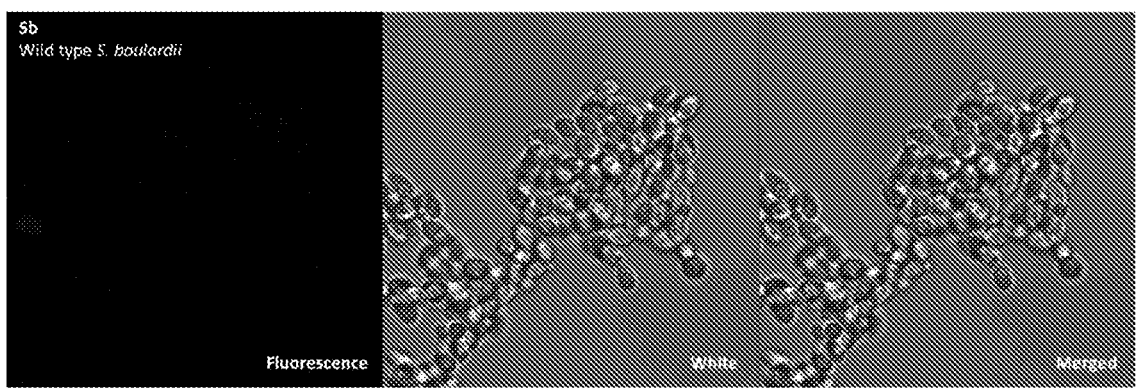
FIG. 7A-FIG. 7D are series of photographs showing immunofluorescence staining and confocal microscopy of wild type *S. boulardii* (FIG. 7A), *S. boulardii* carrying an empty surface display cassette (FIG. 7B), *S. boulardii* carrying a surface display cassette of CLM-1 (FIG. 7C) *S. boulardii* carrying a surface display cassette of CLM-1/FLAG (FIG. 7D).
Figure 7B:
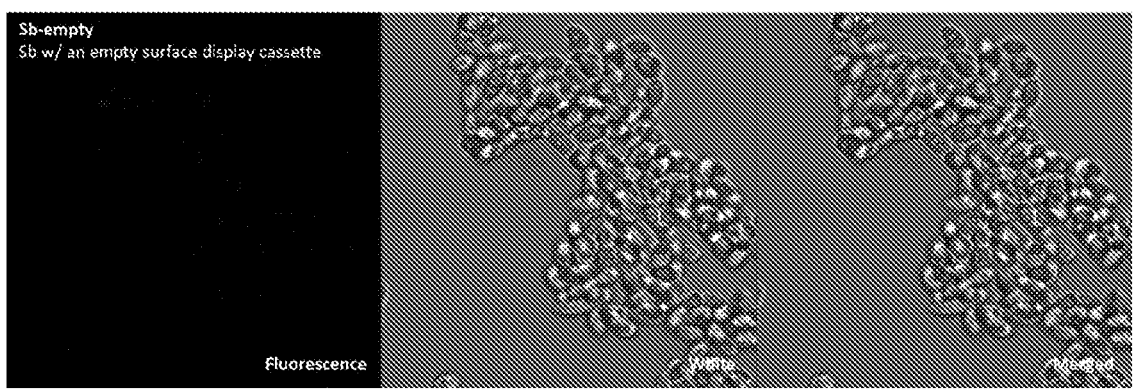
Figure 7C:
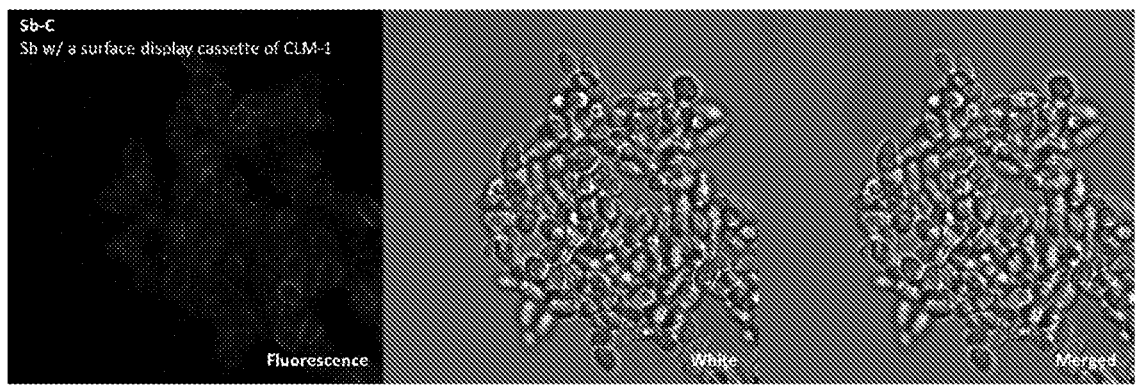
Figure 7D:
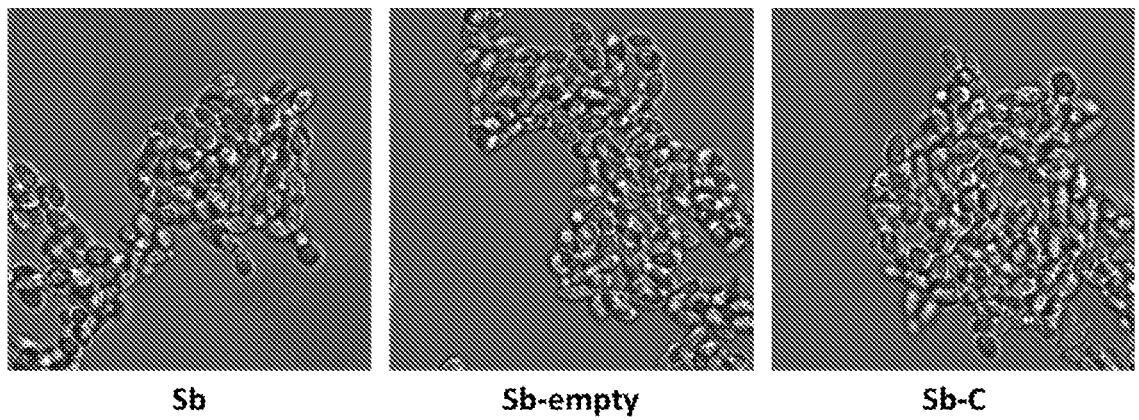
Figure 8:
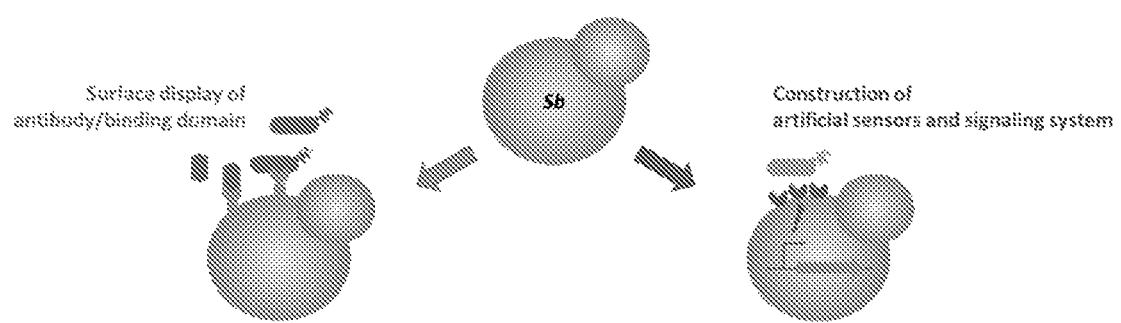
FIG. 8. Design of the construction of artificial sensors and signaling system and surface display of antibody/binding domain.

Cas9-based integration into the IS1n site was used to integrate the surface display cassette into chromosome XV of *S. boulardii*. The CLM-1 display unit expression cassette was bracketed with two homologous regions, which comprise 50 base pairs identical to the upstream and downstream of IS1n, and PCR amplified as a donor DNA for CRISPR-Cas9 genome editing. The donor DNA fragment and the expression vector of the guide RNA that locates Cas9 endonuclease on IS1n were transformed into Cas9-expressing *S. boulardii* (see e.g., FIG. 5). The double strand breakage on IS1n by Cas9 was a selection pressure so that we could select positive constructs that recovered from the double strand breakage by the integration of the donor DNA via homologous recombination covering IS1n. The integration was validated by colony PCR amplifying 500 bp region including the IS1n site (see e.g., FIG. 6) and sequencing. Display of CLM-1 by the display system was validated via immunofluorescence staining and confocal microscopy using Genentech 3F6 (Hamster, non-commercial) and anti-hamster antibody conjugated to fluorophore 647 as primary and secondary antibodies, respectively (see e.g., FIG. 7A-FIG. 7D).

It is believed that this is the first in vivo binding assay, which assessed the effect of the administration of CLM-1-displaying *S. boulardii* on MNOV levels in gut.

Mice who were administered *S. boulardii* shed higher amount of MNOV after administration of *S. boulardii* for 3 days, and MNOV quantities in their stools became lower within 8 days. The effect was significant in the mice who were administered CLM-1-displaying *S. boulardii*.

Norovirus

Norovirus is the leading cause of outbreaks of acute gastroenteritis. MNOV can be grown routinely in cell culture, can infect laboratory mice, and have been used as a system for defining mechanisms of norovirus replication and pathogenesis.

CD300lf

CMRF35-like molecule 1 (CLM-1) was used as the target protein for MNoV. Transmembrane proteins contain a single IgV-like extracellular domain. The CMRF35 antigen, which was identified by reactivity with a monoclonal antibody, is present on monocytes, neutrophils, and some T and B lymphocytes.

Methods

Cell wall binding domains at 3' end region of the endo-lysin genes were amplified without stop codon and substituted the CLM-1-encoding gene in CLM-1-displaying cassette. New display cassettes were also integrated into the intergenic site IS1n through CRISPR-Cas9 genome editing.

Expanding the range of application by using cell wall binding domain derived from phage endolysins can be performed using the methods described herein. For example, display cassettes for LysGH15B and LysSA97 (*S. aureus*), PlyCP26F (*C. difficile/perfringens*), and PlyP35 (*L. monocytogenes*) cell wall binding domains can be constructed. Similarly, cloning of the binding domain of phiCcoIBB35 (*Campylobacter coli*) can be performed in the same manner as the cloning methods for the other cell wall binding domains described herein.

Immunofluorescence Staining and Confocal Microscopy

Target protein was successfully displayed on the surface of *S. boulardii* strains (see e.g., FIGS. 7A-7D). Ring shape of fluorescence signals represent surface display. The primary antibody was Genentech 3F6 targeting CLM-1 protein directly (Hamster, non-commercial). The secondary antibody: anti-hamster antibody conjugated to 647.

Interaction Between CLM-1-Displaying Yeast and MNOV

Figure 13:
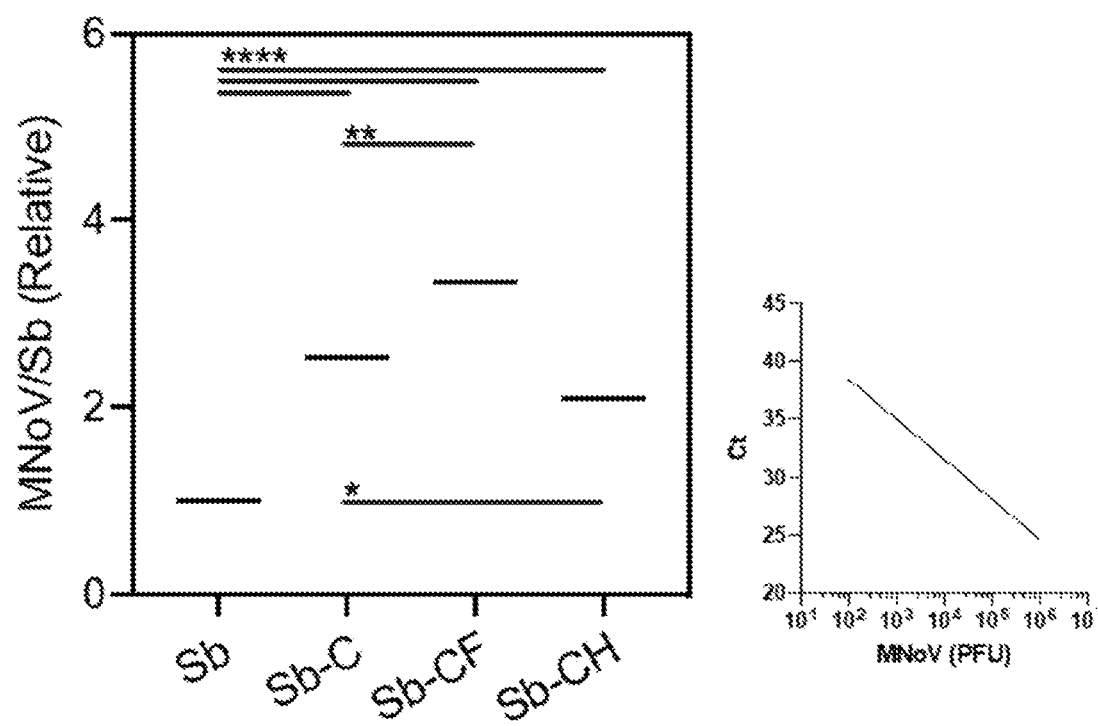
FIG. 13. In vitro binding assay measuring the interaction between CLM-1-displaying *S. boulardii* and MNoV.

An in vitro binding assay (see e.g., FIG. 13) is demonstrated herein.

Quantification of MNOV on the yeast cell surface showed $6*10^8$ CFUs of *S. boulardii* (w/t) or engineered *S. boulardii* (CLM-1-displaying) and $10^6$ plaque forming units (PFUs) of MNOV.

It was shown that the surface display of CLM-1 increases binding capacity of *S. boulardii*. Additional tags between CLM-1 and anchor protein did not significantly affect the interaction.

Figure 14:
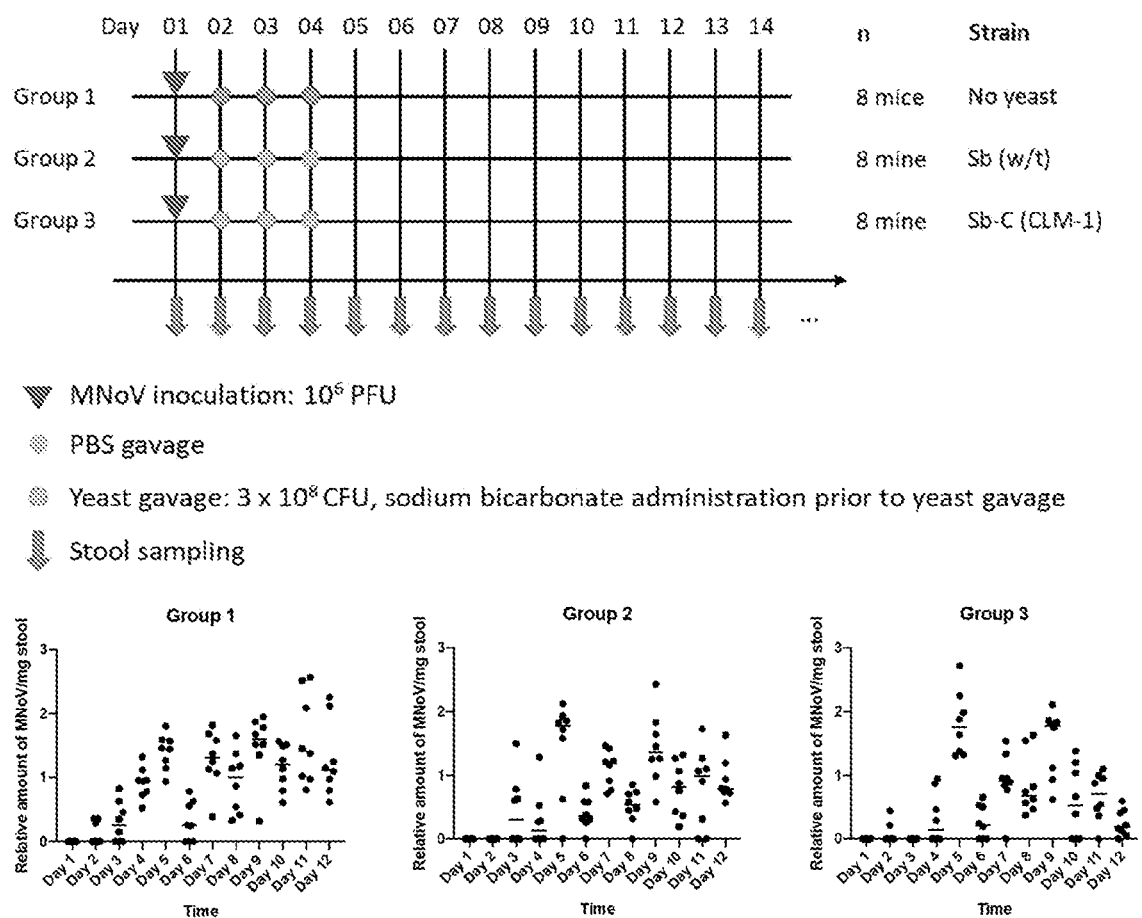
FIG. 14. Study design for measuring the interaction between CLM-1-displaying yeast and MNOV in the mouse gut.

Interaction between CLM-1-displaying yeast and MNOV in the mouse gut was studied (see e.g., FIG. 14 for study design). Mice who were administered *S. boulardii* shed higher amount of MNOV after administration of *S. boulardii* for 3 days, and MNoV quantities in their stools became lower within 8 days. The effect was significant in the mice who were administered CLM-1-displaying *S. boulardii*.

Example 4: In Vivo Stability of Engineered S. Boulardii

This example determined the stability and viability of *S. boulardii* in the mouse gut. It was shown that *S. boulardii* cells were almost cleared from the mouse gut 2 days after discontinuation. This example describes the longevity/sojourn of *S. boulardii* in the mammalian gut in mouse model.

*S. boulardii* passed through mouse gut very quickly (see e.g., FIG. 11A-FIG. 11B). $3 \times 10^8$ CFU live *S. boulardii* was administered to the mouse via oral gavage. A significant amount of Sb cells were found in stools 12 h after gavage (see e.g., FIG. 11A). It was found that *S. boulardii* did not colonize in the mouse gut (see e.g., FIG. 11B).

Figure 12:
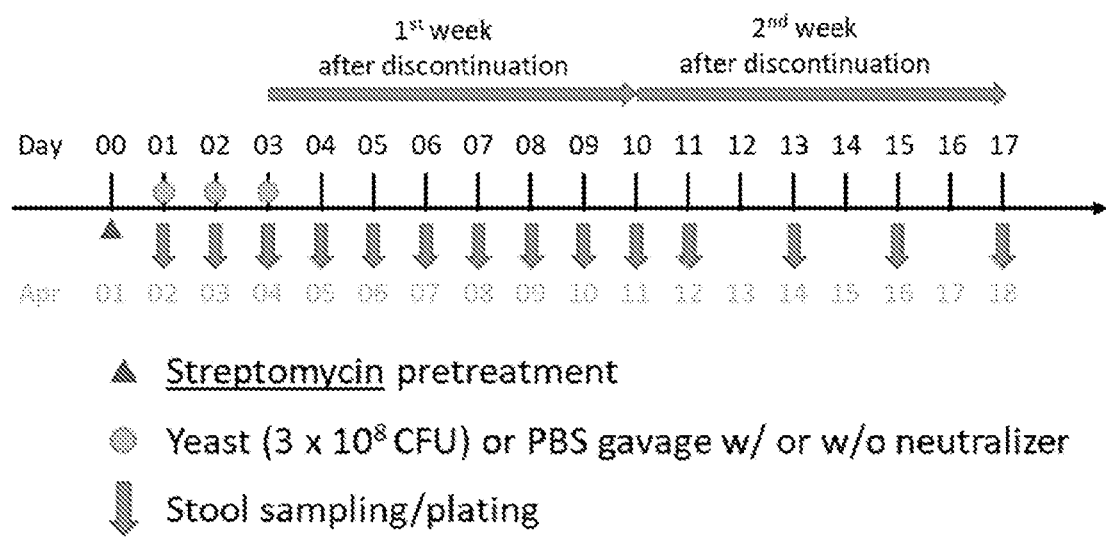
FIG. 12. Effect of multiple administration, perturbation of commensal microbiota (streptomycin), and stomach neutralization on *S. boulardii* stability in the gut.
Figure 12:
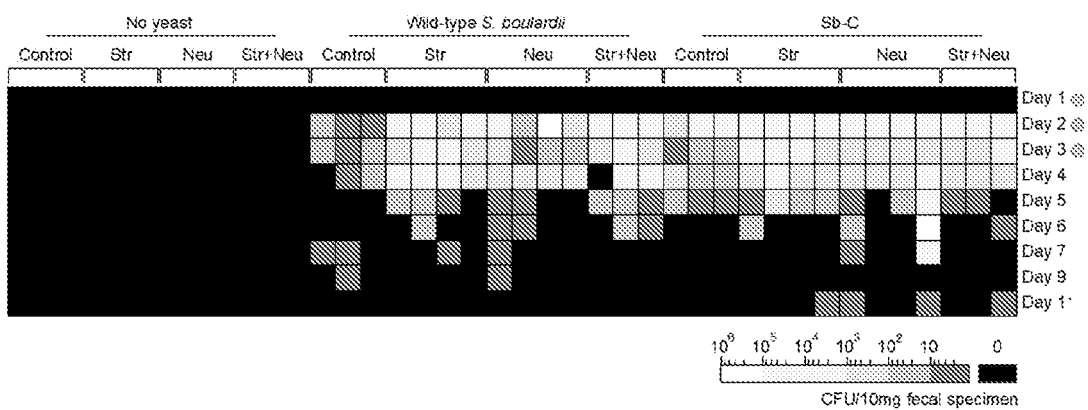

FIG. 12 illustrates the effect of multiple administration, streptomycin, and stomach neutralization. It was shown that both wild-type and engineered *S. boulardii* strains were cleared within 6 days after discontinuation. Streptomycin and sodium bicarbonate did not significantly change viability of *S. boulardii*.

What is claimed is:

1. An engineered *Saccharomyces boulardii* cell comprising a genome-integrated display cassette encoding:
   a. a signal peptide;
   b. a binding agent with binding affinity to a target microorganism selected from the group consisting of norovirus, *Clostridium*, *Listeria*, *Streptococcus*, *Staphylococcus*, and *Campylobacter*;
   c. an anchor comprising a cell wall anchor protein, or a fragment thereof selected from the group consisting of Cwp2p, Sed1p, Ccw12p, Flo1p and Flo428;
   d, wherein (a) is operably linked to (b) which is operably linked to (c);
   wherein the genome integrated display cassette is integrated at any one of a site selected from the group consisting of IS1n, IS2n, IS3n, IS4n, IS5n, and IS6n in the *Saccharomyces boulardii* genome; and
   wherein the target microorganism is norovirus and the binding agent is CLM-1; the target microorganism is *Clostridium difficile* or *Clostridium perfringens* and the binding agent is a cell binding domain of ΦCP26F; the target microorganism is *Listeria monocytogenes* and the binding agent is cell binding domain 500 of endolysin Ply500 or cell wall binding domain of PlyP35; the target microorganism is *Streptococcus pyogenes* and the binding agent is PlyC binding domain of endolysin PlyC; the target microorganism is methicillin-resistant *Staphylococcus aureus* (MRSA) or *Staphylococcus aureus* and the binding agent is LysGH15B, a cell wall binding domain of endolysin LysGH15, LysSA97, or ZW88; or the target microorganism is *Campylobacter coli* and the binding agent is a cell wall binding domain of phiCcoIBB35.

2. The engineered *Saccharomyces boulardii* cell of claim 1, further comprising a second binding agent, wherein the second binding agent binds a second target microorganism and the binding agent is different from the second binding agent.

3. The engineered *Saccharomyces boulardii* cell of claim 1, wherein the binding agent comprises one or more of the group consisting of peptides, proteins, antibodies, nanobodies, single chain fragments thereof, and combinations thereof.

4. The engineered *Saccharomyces boulardii* cell of claim 1, wherein the binding agent comprises one or more of the group consisting of: a cell wall binding domain of a target microorganism and a cell wall binding domain of an endolysin.

5. The engineered *Saccharomyces boulardii* cell of claim 1, wherein the anchor protein comprises a cell wall protein anchor region in a single cistron operably linked to a promoter and a terminator.

6. The engineered *Saccharomyces boulardii* cell of claim 1, wherein the target microorganism is norovirus and the binding agent is CLM-1.

7. The engineered *Saccharomyces boulardii* cell of claim 1, wherein the target microorganism is *Clostridium difficile* or *Clostridium perfringens* and the binding agent is a cell binding domain of ΦCP26F.

8. The engineered *Saccharomyces boulardii* cell of claim 1, wherein the target microorganism is *Listeria monocytogenes* and the binding agent is cell binding domain 500 of endolysin Ply500 or cell wall binding domain of PlyP35.

9. The engineered *Saccharomyces boulardii* cell of claim 1, wherein the target microorganism is *Streptococcus pyogenes* and the binding agent is PlyC binding domain of endolysin PlyC.

10. The engineered *Saccharomyces boulardii* cell of claim 1, wherein the target microorganism is methicillin-resistant *Staphylococcus aureus* (MRSA) or *Staphylococcus aureus* and the binding agent is LysGH15B, a cell wall binding domain of endolysin LysGH15, LysSA97, or ZW88.

11. The engineered *Saccharomyces boulardii* cell of claim 1, the target microorganism is *Campylobacter coli* and the binding agent is a cell wall binding domain of phiCcoIBB35.

12. The engineered *Saccharomyces boulardii* cell of claim 1, wherein the engineered *Saccharomyces* cell comprises a reporter gene.

13. The engineered *Saccharomyces boulardii* cell of claim 12, wherein the reporter gene is selected from the group consisting of GFP, RFP, BFP, luminescence proteins, and combinations thereof.

14. A method of targeted sensing, detecting, or killing of commensal or pathogenic gut microbes comprising administering a therapeutically effective amount of the engineered *Saccharomyces* cell of claim 1.

15. A method of constructing an engineered *Saccharomyces* cell of claim 1 comprising:
    providing a *Saccharomyces* cell;
    providing a display cassette; and
    integrating the display cassette into an intergenic site of the *Saccharomyces* cell genome.

16. The method of claim 15, wherein a-c are in a single cistron bracketed by a constitutive promoter and a terminator.

17. The method of claim 16, wherein the cell wall anchor protein is selected from Cwp2p, Sed1p, Ccw12p, or Flo1p.

18. The method of claim 15, wherein the cell wall anchor protein is from Flo1p, or a fragment thereof.

19. The method of claim 15, wherein the binding agent comprises one or more of the group consisting of: a cell wall binding domain of a target microorganism and a cell wall binding domain of an endolysin.

20. The method of claim 15 wherein the binding agent is selected from CLM-1; ZW88; cell binding domain of ΦCP26F (PlyCP26F); cell binding domain 500 of endolysin Ply500; PlyC binding domain of endolysin PlyC; LysGH15B, a cell wall binding domain of endolysin LysGH15 or LysSA97; or cell wall binding domain of phiCcoIBB35.

21. The method of claim 15, wherein the *Saccharomyces* cell is from *S. boulardii* and the intergenic site is selected from Chr VII, XII, XV, or XVI, or a combination thereof.

22. The method of claim 16, comprising a strong constitutive promoter or weak promoter of the engineered microorganism.

23. The method of claim 22, wherein the strong constitutive promoter is selected from the group consisting of TDH3 CCW12, ADH1, and TEF1 promoters of *S. boulardii*.

24. The method of claim 22, wherein the weak promoter is selected from the group consisting of WSC1 and FAU1 promoters of *S. boulardii*.

25. The method of claim 16, wherein the terminator is selected from the group consisting of ADH1 and CYC1 terminators of *S. boulardii*.

26. The engineered *Saccharomyces boulardii* cell of claim 5, wherein the *S. boulardii* promoter is selected from the group consisting of TDH3, CCW12, ADH1, TEF1, WSC1 and FAU1.

27. The engineered *Saccharomyces boulardii* cell of claim 5, wherein the *S. boulardii* terminator is selected from the group consisting of ADH1 and CYC1.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Saccharomyces boulardii

<400> SEQUENCE: 1
ttggcaacta ctctcaaagg                                                    20

<210> SEQ ID NO 2
<211> LENGTH: 20
<212> TYPE: DNA
<213> ORGANISM: Saccharomyces boulardii

<400> SEQUENCE: 2
gtaaggaatt atgttcgccc                                                    20

<210> SEQ ID NO 3
<211> LENGTH: 20
<212> TYPE: DNA
<213> ORGANISM: Saccharomyces boulardii

<400> SEQUENCE: 3
gttgtcaatt gccacagagg                                                    20

<210> SEQ ID NO 4
<211> LENGTH: 20
<212> TYPE: DNA
<213> ORGANISM: Saccharomyces boulardii

<400> SEQUENCE: 4
gggaaagttt gaaaatgtgg                                                    20

<210> SEQ ID NO 5
<211> LENGTH: 20
<212> TYPE: DNA
<213> ORGANISM: Saccharomyces boulardii

<400> SEQUENCE: 5
tcctctacaa cccaatgagg                                                    20

<210> SEQ ID NO 6
<211> LENGTH: 20
<212> TYPE: DNA
<213> ORGANISM: Saccharomyces boulardii

<400> SEQUENCE: 6
gtagggagct actacaaagt                                                    20

<210> SEQ ID NO 7
<211> LENGTH: 23
<212> TYPE: DNA
<213> ORGANISM: Artificial Sequence
<220> FEATURE:
<223> OTHER INFORMATION: PtetO PAM/scRNA binding sequence

<400> SEQUENCE: 7
gggatagtca ctatctcttt tca                                                23

<210> SEQ ID NO 8
<211> LENGTH: 23
<212> TYPE: DNA
<213> ORGANISM: Artificial Sequence

```
<220> FEATURE:
<223> OTHER INFORMATION: PGALsyn1 PAM/scRNA binding sequence

<400> SEQUENCE: 8
atctgtcgac agtgcgatac agg                                         23

<210> SEQ ID NO 9
<211> LENGTH: 23
<212> TYPE: DNA
<213> ORGANISM: Artificial Sequence
<220> FEATURE:
<223> OTHER INFORMATION: PGALsyn2 PAM/scRNA binding sequence

<400> SEQUENCE: 9
cgcgaactcg agaccgaagg ggg                                         23

<210> SEQ ID NO 10
<211> LENGTH: 23
<212> TYPE: DNA
<213> ORGANISM: Artificial Sequence
<220> FEATURE:
<223> OTHER INFORMATION: PGALsyn3 PAM/scRNA binding sequence

<400> SEQUENCE: 10
ttaggtgcta cgtcacgagc tgg                                         23

<210> SEQ ID NO 11
<211> LENGTH: 23
<212> TYPE: DNA
<213> ORGANISM: Artificial Sequence
<220> FEATURE:
<223> OTHER INFORMATION: PGALsyn4 PAM/scRNA binding sequence

<400> SEQUENCE: 11
ttcaacgcgt tcacgtgtgg tgg                                         23

<210> SEQ ID NO 12
<211> LENGTH: 23
<212> TYPE: DNA
<213> ORGANISM: Artificial Sequence
<220> FEATURE:
<223> OTHER INFORMATION: PGALsyn5 PAM/scRNA binding sequence

<400> SEQUENCE: 12
tctctatcac tgatagggag cgg                                         23
```